United States Patent
Landers et al.

(10) Patent No.: US 10,198,286 B2
(45) Date of Patent: Feb. 5, 2019

(54) HANDLING MEMORY REQUESTS

(71) Applicant: Imagination Technologies Limited, Kings Langley (GB)

(72) Inventors: Mark Landers, Hertfordshire (GB); Martin John Robinson, Hertfordshire (GB)

(73) Assignee: Imagination Technologies Limited, Kings Langley (GB)

( * ) Notice: Subject to any disclaimer, the term of this patent is extended or adjusted under 35 U.S.C. 154(b) by 121 days.

(21) Appl. No.: 15/471,256

(22) Filed: Mar. 28, 2017

(65) Prior Publication Data

US 2017/0286151 A1  Oct. 5, 2017

(30) Foreign Application Priority Data

Mar. 29, 2016  (GB) .................................. 1605243.3

(51) Int. Cl.
*G06F 9/46* (2006.01)
*G06F 9/455* (2018.01)
(Continued)

(52) U.S. Cl.
CPC .......... *G06F 9/467* (2013.01); *G06F 9/45558* (2013.01); *G06F 12/0811* (2013.01);
(Continued)

(58) Field of Classification Search
CPC .. G06F 9/467; G06F 9/45558; G06F 12/0811; G06F 12/0831; G06F 12/0891; G06F 12/0897
See application file for complete search history.

(56) References Cited

U.S. PATENT DOCUMENTS 5,933,844 A     8/1999  Young
6,330,630 B1 * 12/2001  Bell .................... G06F 13/4027
                                                 710/312
(Continued)

FOREIGN PATENT DOCUMENTS

WO        00/22532 A1    4/2000

OTHER PUBLICATIONS

EPO. Search Opinion, dated Oct. 8, 2017. pp. 1-4. (Year: 2017).*

*Primary Examiner* — Ryan Bertram
(74) *Attorney, Agent, or Firm* — Vorys, Sater, Seymour and Pease LLP; Vincent M DeLuca

(57) ABSTRACT

A converter module is described which handles memory requests issued by a cache (e.g. an on-chip cache), where these memory requests include memory addresses defined within a virtual memory space. The converter module receives these requests, issues each request with a transaction identifier and uses that identifier to track the status of the memory request. The converter module sends requests for address translation to a memory management unit and where there the translation is not available in the memory management unit receives further memory requests from the memory management unit. The memory requests are issued to a memory via a bus and the transaction identifier for a request is freed once the response has been received from the memory. When issuing memory requests onto the bus, memory requests received from the memory management unit may be prioritized over those received from the cache.

20 Claims, 11 Drawing Sheets

(51) Int. Cl.
*G06F 12/0811* (2016.01)
*G06F 12/0831* (2016.01)
*G06F 12/0891* (2016.01)
*G06F 12/1045* (2016.01)
*G06F 13/16* (2006.01)
*G06F 12/0897* (2016.01)
*G06F 12/1027* (2016.01)

(52) U.S. Cl.
CPC ...... *G06F 12/0831* (2013.01); *G06F 12/0891* (2013.01); *G06F 12/0897* (2013.01); *G06F 12/1027* (2013.01); *G06F 12/1063* (2013.01); *G06F 13/1605* (2013.01); *G06F 13/1684* (2013.01); *G06F 2009/45583* (2013.01); *G06F 2212/1008* (2013.01); *G06F 2212/1024* (2013.01); *G06F 2212/60* (2013.01); *G06F 2212/621* (2013.01); *G06F 2212/684* (2013.01)

(56) References Cited

U.S. PATENT DOCUMENTS

| | | | |
|---|---|---|---|
| 2004/0143704 A1* | 7/2004 | Vo | G06F 13/1652 711/118 |
| 2007/0055827 A1* | 3/2007 | Tsien | G06F 12/0831 711/141 |
| 2007/0101044 A1 | 5/2007 | Sudheer | |
| 2008/0140919 A1 | 6/2008 | Torabi et al. | |
| 2009/0198893 A1* | 8/2009 | Sorgard | G06F 12/1027 711/118 |
| 2011/0087858 A1 | 4/2011 | Persson et al. | |
| 2011/0296110 A1* | 12/2011 | Lilly | G06F 13/1668 711/118 |
| 2015/0052304 A1* | 2/2015 | Avudaiyappan | G06F 12/0888 711/122 |
| 2017/0206165 A1* | 7/2017 | Lim | G11C 8/08 |

* cited by examiner

HANDLING MEMORY REQUESTS

BACKGROUND

In order to reduce the latency associated with accessing data stored in main memory, processors (such as CPUs or GPUs) typically have one or more caches, as shown in the example memory hierarchy 100 in FIG. 1. There are typically two levels of on-chip cache, L1 102 and L2 104 which are usually implemented with SRAM (static random access memory). The caches are smaller than the main memory 108, which may be implemented in DRAM (dynamic random access memory), but the latency involved with accessing a cache is much shorter than for main memory, and gets shorter at lower levels within the hierarchy (i.e. closer to the processor). As the latency is related, at least approximately, to the size of the cache, a lower level cache (e.g. L1) is smaller than a higher level cache (e.g. L2).

When a processor accesses a data item, the data item is accessed from the lowest level in the hierarchy where it is available. For example, a look-up will be performed in the L1 cache 102 and if the data is in the L1 cache, this is referred to as a cache hit and the data can be loaded into one of the registers 110. If however, the data is not in the L1 cache (the lowest level cache), this is a cache miss and the next levels in the hierarchy are checked in turn until the data is found (e.g. L2 cache 104 is checked in the event of a L1 cache miss). In the event of a cache miss, the data is brought into the cache (e.g. the L1 cache 102) and if the cache is already full, a replacement algorithm may be used to decide which existing data will be evicted (i.e. removed) in order that the new data can be stored.

If a data item is not in any of the on-chip caches (e.g. not in the L1 cache 102 or the L2 cache 104 in the hierarchy shown in FIG. 1), then a memory request is issued onto an external bus (which may also be referred to as the interconnect fabric) so that the data item can be obtained from the next level in the hierarchy (e.g. the main memory 108).

The embodiments described below are provided by way of example only and are not limiting of implementations which solve any or all of the disadvantages of known methods of managing access to memory.

SUMMARY OF THE INVENTION

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

A converter module is described which handles memory requests issued by a cache (e.g. an on-chip cache), where these memory requests include memory addresses defined within a virtual memory space. The converter module receives these requests, issues each request with a transaction identifier and uses that identifier to track the status of the memory request. The converter module sends requests for address translation to a memory management unit and where there the translation is not available in the memory management unit receives further memory requests from the memory management unit. The memory requests are issued to a memory via a bus and the transaction identifier for a request is freed once the response has been received from the memory. When issuing memory requests onto the bus, memory requests received from the memory management unit may be prioritized over those received from the cache.

A first aspect provides a module comprising: an assignment module arranged to receive memory requests from a cache and to assign a transaction identifier to each received memory request, wherein the memory requests received from the cache include one or more memory addresses defined in a virtual address space; a transaction tracker module arranged to receive a memory request from the assignment module with the assigned transaction identifier, to track the status of the memory request and to receive translation information from a memory management unit, wherein the translation information comprises a translation of a virtual memory address in the memory request to a physical memory address or a pointer to the translation; and an arbiter module arranged to receive a memory request from the transaction tracker module with the assigned transaction identifier when the memory request is ready for issue and to issue the memory request to a memory via an external bus and to trigger the freeing of the assigned transaction identifier in response to receiving a response from the memory via the external bus, wherein the memory request issued to memory includes one or more physical memory addresses determined using the translation information.

A second aspect provides a method comprising: receiving memory requests from a cache at a converter module; assigning, in the converter module, a transaction identifier to each received memory request, wherein the memory requests received from the cache include one or more memory addresses defined in a virtual address space; tracking, in the converter module, the status of the memory requests; receiving, in the converter module, translation information from a memory management unit, wherein the translation information comprises a translation of a virtual memory address in one of the memory requests to a physical memory address or a pointer to the translation; issuing said one of the memory requests from the converter module to a memory via an external bus, wherein the memory request issued to memory includes one or more physical memory addresses determined using the translation information; and triggering the freeing of the assigned transaction identifier in response to receiving a response from the memory via the external bus.

Further aspects provide a processing system configured to perform the method described herein, a processing system comprising a module as described herein embodied in hardware on an integrated circuit, computer readable code adapted to perform the steps of the method described herein when the code is run on a computer, a method of manufacturing, at an integrated circuit manufacturing system, a processing system comprising a module as described herein, an integrated circuit definition dataset that, when processed in an integrated circuit manufacturing system, configures the system to manufacture a processing system comprising a module as described herein, a computer readable storage medium having stored thereon a computer readable description of an integrated circuit that, when processed in an integrated circuit manufacturing system, causes the integrated circuit manufacturing system to manufacture a processing system comprising a module as described herein, and an integrated circuit manufacturing system comprising: a non-transitory computer readable storage medium having stored thereon a computer readable description of an integrated circuit that describes a graphics processing system; a layout processing system configured to process the integrated circuit description so as to generate a circuit layout description of an integrated circuit embodying the graphics processing system; and an integrated circuit generation system configured to manufacture the graphics processing system according to the circuit layout description, wherein the processing system comprises a module as described herein.

The converter module may be embodied in hardware on an integrated circuit. There may be provided a method of manufacturing, at an integrated circuit manufacturing system, a converter module and/or a processor comprising a converter module. There may be provided an integrated circuit definition dataset that, when processed in an integrated circuit manufacturing system, configures the system to manufacture a converter module and/or a processor comprising a converter module. There may be provided a non-transitory computer readable storage medium having stored thereon a computer readable description of an integrated circuit that, when processed, causes a layout processing system to generate a circuit layout description used in an integrated circuit manufacturing system to manufacture a converter module and/or a processor comprising a converter module.

There may be provided an integrated circuit manufacturing system comprising: a non-transitory computer readable storage medium having stored thereon a computer readable integrated circuit description that describes the converter module and/or a processor comprising the converter module; a layout processing system configured to process the integrated circuit description so as to generate a circuit layout description of an integrated circuit embodying the converter module and/or a processor comprising the converter module; and an integrated circuit generation system configured to manufacture the converter module and/or a processor comprising the converter module according to the circuit layout description.

There may be provided computer program code for performing a method as described herein. There may be provided non-transitory computer readable storage medium having stored thereon computer readable instructions that, when executed at a computer system, cause the computer system to perform the method as described herein.

The preferred features may be combined as appropriate, as would be apparent to a skilled person, and may be combined with any of the aspects of the invention.

BRIEF DESCRIPTION OF THE DRAWINGS

Embodiments of the invention will be described, by way of example, with reference to the following drawings, in which.

Figure 1:
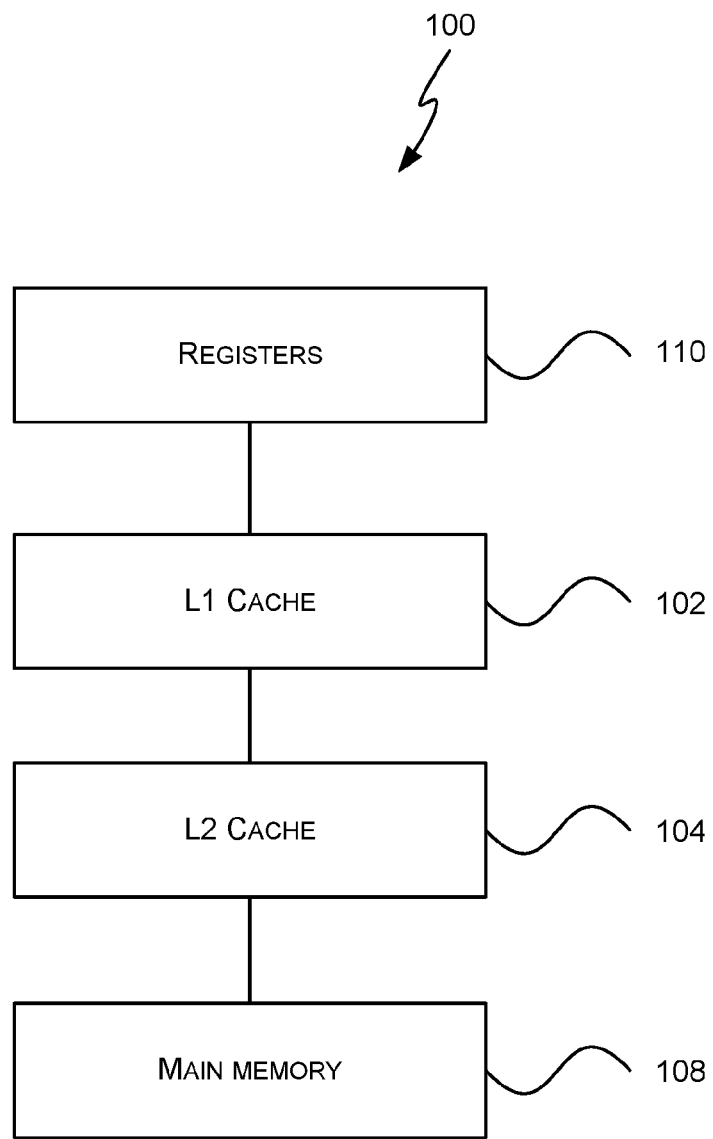
FIG. 1 is a schematic diagram of an example memory hierarchy.

The accompanying drawings illustrate various examples. The skilled person will appreciate that the illustrated element boundaries (e.g., boxes, groups of boxes, or other shapes) in the drawings represent one example of the boundaries. It may be that in some examples, one element may be designed as multiple elements or that multiple elements may be designed as one element. Common reference numerals are used throughout the figures to indicate similar features.

DETAILED DESCRIPTION

The following description is presented by way of example to enable a person skilled in the art to make and use the invention. The present invention is not limited to the embodiments described herein and various modifications to the disclosed embodiments will be apparent to those skilled in the art.

Embodiments will now be described by way of example only.

Described herein is a converter module (which may also be referred to as an interface module) which is located between a cache (which may be referred to as an on-chip cache as it is a cache which is on the same chip as the processor, is connected via an internal bus and is considered to be within the processor core, such as the L2 cache 104 in the hierarchy 100 shown in FIG. 1) and a memory (which may be referred to as an off-chip memory as it is a memory which is connected via an external bus, such as the main memory 108 in the hierarchy 100 shown in FIG. 1). The converter module receives memory requests from the on-chip cache (via the internal bus) and issues memory requests onto an external bus so that they can be received by the off-chip memory. Whilst the following description refers to the cache as 'on-chip' and the memory as 'off-chip', this is by way of example only and in various implementations both the cache and memory may be implemented within a single system on chip (e.g. on the same piece of silicon) or within a single package.

As described in more detail below, the converter module is connected to a MMU (memory management unit) which translates between virtual memory addresses and physical memory addresses. In systems which use the converter module described herein, the on-chip caches therefore operate in virtual memory address space and generate requests to memory in virtual memory address space. The converter module described herein converts these memory requests into a protocol used on the external bus which is in physical address space (e.g. AXI 4 ACE protocol, Open Core Protocol, OCP, or a proprietary protocol). The protocol used on the external bus is typically more heavyweight than that used on the internal bus (which is typically a proprietary protocol) and whilst the external bus generally operates out-of-order and may have multiple channels for performance reasons, the internal bus usually operates in-order. In the event of a miss in the MMU (i.e. because the required translation is not stored in a translation lookaside buffer, TLB, in the MMU), the MMU also generates a memory request and these memory requests are also issued onto the external bus by the converter module.

By performing the address translation on the output of the cache (i.e. using the converter module described herein), it is possible to absorb a large amount of the translation latency. If instead the translations are performed before the cache (e.g. on the input to the cache), it may require the processor to be stalled whilst a translation is performed, because translations can be very slow. Additionally it reduces the volume of requests into the MMU which may reduce power consumption and as the buses between the L1 and L2 cache are no longer subject to MMU misses (as they are both working in the virtual memory address space), these may maintain higher efficiency/utilization (e.g. as the L2 cache will tend to absorb requests without stalling back, providing sufficient transaction IDs are supported).

As well as triggering address translation (from virtual to physical address space using the MMU), the converter module assigns transaction identifiers (IDs) to the incoming memory requests received from the on-chip cache and tracks each transaction which is outstanding (i.e. which has been received but is not yet complete). Transaction IDs are freed up so that they can be re-used (i.e. assigned to another incoming memory request) once a transaction is complete. A separate set of transaction IDs may be used when assigning transaction IDs to the memory requests that result from MMU/TLB misses. These transaction IDs are separate and distinct from any IDs which are allocated by the external bus and which allow the bus to also do re-ordering.

The assignment of a transaction ID and the tracking of the IDs enables the memory requests to be performed out-of-order, i.e. they may be issued onto the external bus out-of-order and responses do not need to be re-ordered when they are received by the converter module before passing data back to the on-chip cache (i.e. the data may be passed back to the MMU or on-chip cache in the order that it returns). The converter module uses one or more rules to select which transactions are issued next onto the external bus and these rules (along with the ability to issue requests onto the external bus out-of-order) enable MMU/TLB misses to be prioritized and the latency associated with such misses to be hidden (e.g. because other transactions can be issued whilst waiting for a MMU/TLB miss to return).

Figure 2:
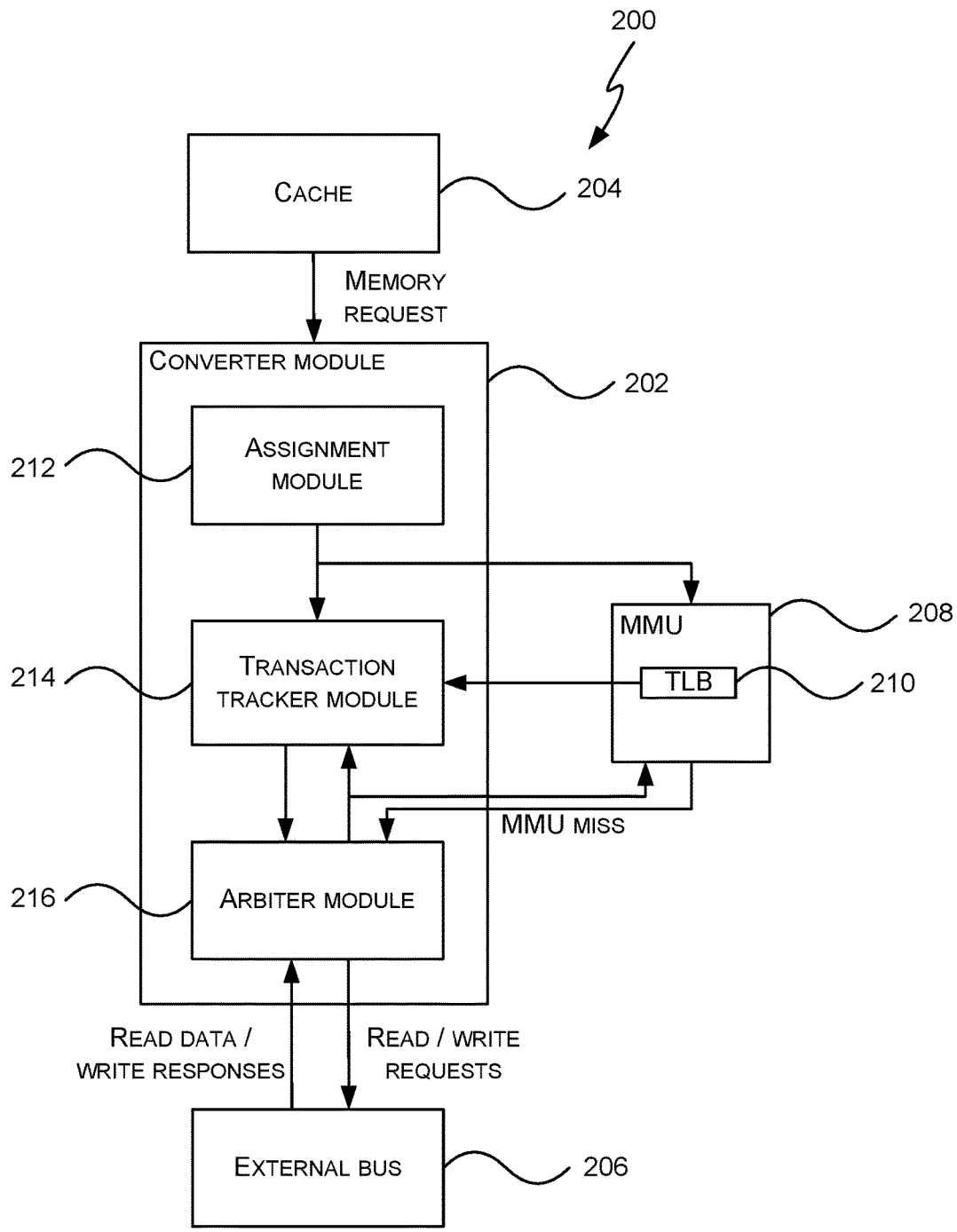
FIG. 2 is a schematic diagram of part of a memory hierarchy including a first example converter module.

FIG. 2 is a schematic diagram 200 of part of a memory hierarchy including a converter module 202 which receives memory requests from an on-chip cache 204 which is the furthest from the processor (i.e. the last cache in the hierarchy before the external bus, which may also be referred to as the last on-chip cache e.g. an L2 cache) and issues memory requests to the next memory in the hierarchy (e.g. the main memory 108 in the example of FIG. 1) via an external bus 206 (to which the off-chip memory is connected). The converter module 202 is connected to a MMU 208 which comprises a TLB 210. The memory requests which are received by the converter module 202 may be a consequence of a cache miss (i.e. a miss in the cache from which the request is received), a cache eviction or a cache maintenance operation (e.g. a cache flush). Where the cache supports bypass accesses, the converter may also receive write requests from the cache that have passed through the cache unchanged.

The converter module 202 comprises an assignment module 212 which receives the read/write requests from the cache 204 and assigns transaction IDs to those requests. The converter module 202 also comprises a transaction tracker module 214 which tracks each incoming read/write request using the transaction ID assigned by the assignment module 212, e.g. to determine whether the translation is available in the TLB and so whether the request can be issued.

The assignment module 212 or the transaction tracker module 214 may send a translation request to the MMU 208 for each memory request received from the cache 204. These translation requests are tagged with the transaction ID of the corresponding memory request. In response to a translation request, the MMU 208 returns the translation or a pointer to the translation to the transaction tracker module 214 along with the transaction ID (so that the transaction tracker module 214 can match up translations/translation pointers and corresponding memory requests). In the event of a MMU hit, the translation/translation pointer can be returned straight away; however, in the event of a MMU/TLB miss (i.e. where a translation is not stored in the TLB 210) the MMU generates a further memory request and waits for the data to be returned before it can return the translation/translation pointer for the particular transaction ID. If the MMU uses nested translations, it may be necessary to make several calls to memory (i.e. to issue several memory requests) before the translation/translation pointer can be returned to the transaction tracker module 214 and this results in several cycles of latency.

As described above, the latency which results from a MMU/TLB miss can be minimized by prioritizing (in an arbiter module 216) MMU requests over cache originating requests. The latency can also be at least partially hidden by issuing memory requests out-of-order such that other memory requests can still be issued and are not stalled whilst the translation is retrieved.

The converter module 202 further comprises an arbiter module 216 which receives memory requests which are ready to be issued from both the transaction tracker module 214 and the MMU 208. The requests that are received from the transaction tracker module 214 originate from the cache 202 but now include the physical address which was obtained from the TLB (instead of the virtual memory address). The requests that are received from the MMU 208 are generated by the MMU in response to a MMU/TLB miss (as described above).

The arbiter module 216 selects one or more of memory requests it receives each clock cycle and issues them onto the external bus 206. The arbiter module 216 uses one or more rules to determine which memory request to select and issue at any time (e.g. the highest priority transaction request may be selected), rather than working in transaction ID order. In the event that more memory requests are ready to be issued than can be issued onto the external bus 206, those memory requests which are waiting to be issued may be buffered within the arbiter module 216 or may remain in an output state where they are waiting to be selected by the arbiter module 216.

In various examples the arbiter module 216 may prioritise memory requests that were generated by the MMU 208 (as a consequence of a MMU/TLB miss) over memory requests that were generated by the cache 204. This reduces the latency associated with a MMU/TLB miss. If there are no memory requests that were generated by the MMU 208, the memory requests generated by the cache 204 may be selected in order of MMU hits (i.e. in the order that the translations in TLB are available), however, the arbiter module 216 may also attempt to issue memory requests from the cache 204 in age order wherever possible (e.g. if there are two memory requests from the cache where the translation is available, the oldest one may be selected to be issued onto the external bus 206).

The arbiter module 216 also receives read data and write responses back from the external bus 206 and these may be received back in an order which is different to the order in which the memory requests were issued onto the external bus 206 by the arbiter module 216. However, the read data and write responses which are received are accompanied by the corresponding transaction ID and so the arbiter module 216 can determine whether the response corresponds to a request issued by the cache 204 or the MMU 208. Where the response corresponds to a request issued by the MMU 208, the response (e.g. the read data) is passed to the MMU 208. Where the response corresponds to a request issued by the cache 204, the response (which may be read data or a write response) is passed to the transaction tracker module 214 and then on to the cache.

The tracking of an incoming read/write request in the transaction tracker module 214 may comprise storing the current state of each transaction and updated the stored state when the status of a transaction changes (e.g. according to a state diagram which details the possible transitions from state to state and the conditions required for a transition to occur). For example, an available transaction ID may initially be in an IDLE state. When the transaction ID is allocated to an incoming read/write transaction (by the assignment module 212) and the translation is requested, the state may be updated to a TRANSLATING state. When the translation (or a pointer to the translation) is returned by the MMU 208, the state of the transaction may be updated to an OUTPUT state. Once in the OUTPUT state, a transaction can be selected by the arbiter module 216 for issuance onto the external bus 206. Once issued, the transaction is updated to an AWAIT DATA state for a read transaction or an AWAIT RESPONSE state for a write transaction and then once the read data or write response has been received and the transaction ID freed, the state returns to the IDLE state, indicating that the transaction ID can be reallocated to a new incoming memory request.

It will be appreciated that in order for a write request to be ready for issue (and hence moved to the OUTPUT state), the data to be written must also be available. The write data may be provided by a separate path within the converter module 202 (not shown in FIG. 2) which comprises an output write data buffer (OWDB). The write data is stored in the OWDB when received and the index/address of the write data in the OWDB is provided to the transaction tracker module 214 once available. Once both the translation and the write data are available, a write request is ready to be issued and can be passed to the arbiter module 216 (along with both the transaction ID and the OWDB index). Once a write request is selected by the arbiter, the index and burst length is then sent to the OWDB so that the required data to accompany the write command can then be read out of the OWDB using the index as a start address and the burst length to determine the number of words of data.

Figure 3A:
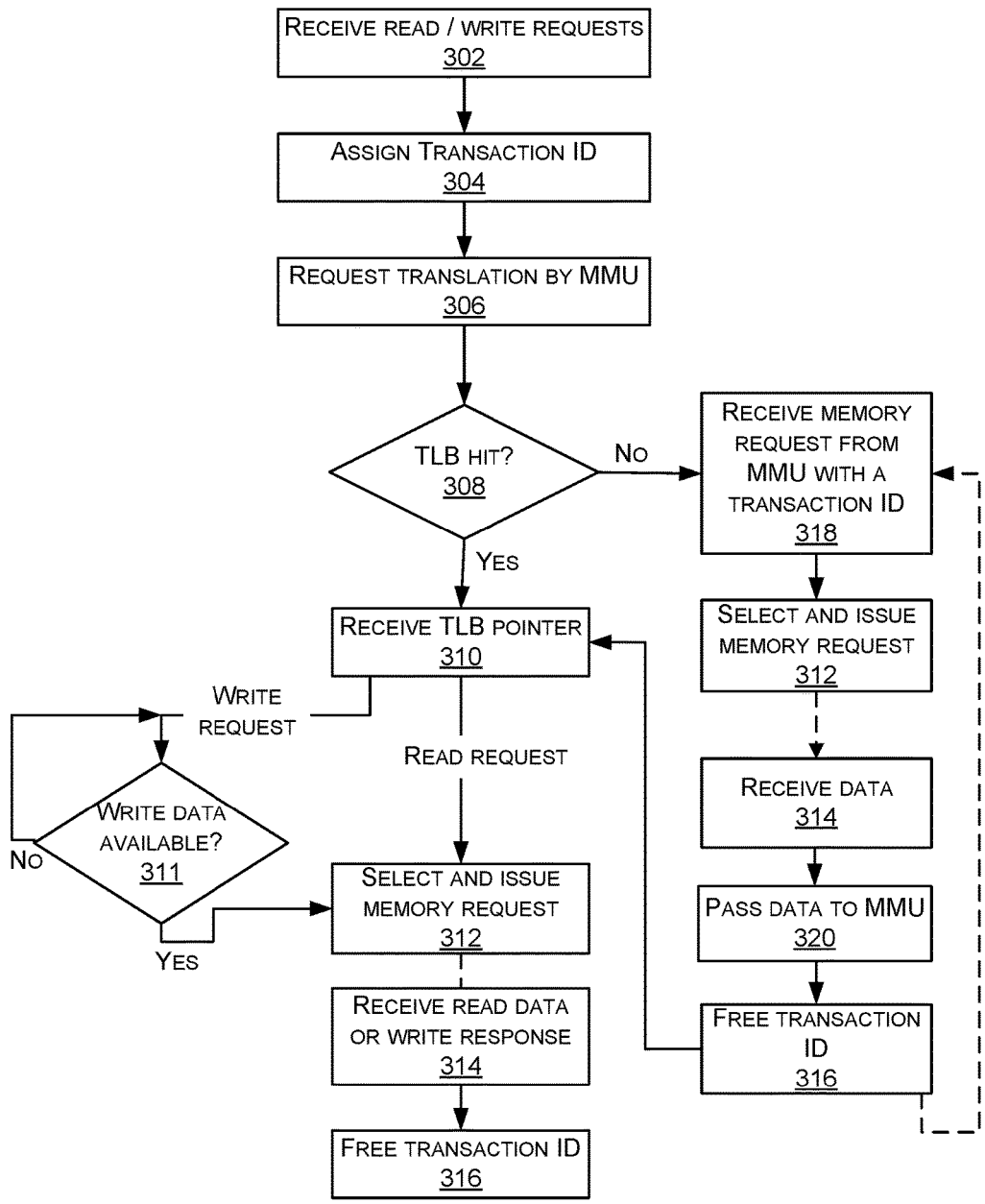
FIG. 3A is a flow diagram showing a first example method of operation of a converter module as described herein.
Figure 3B:
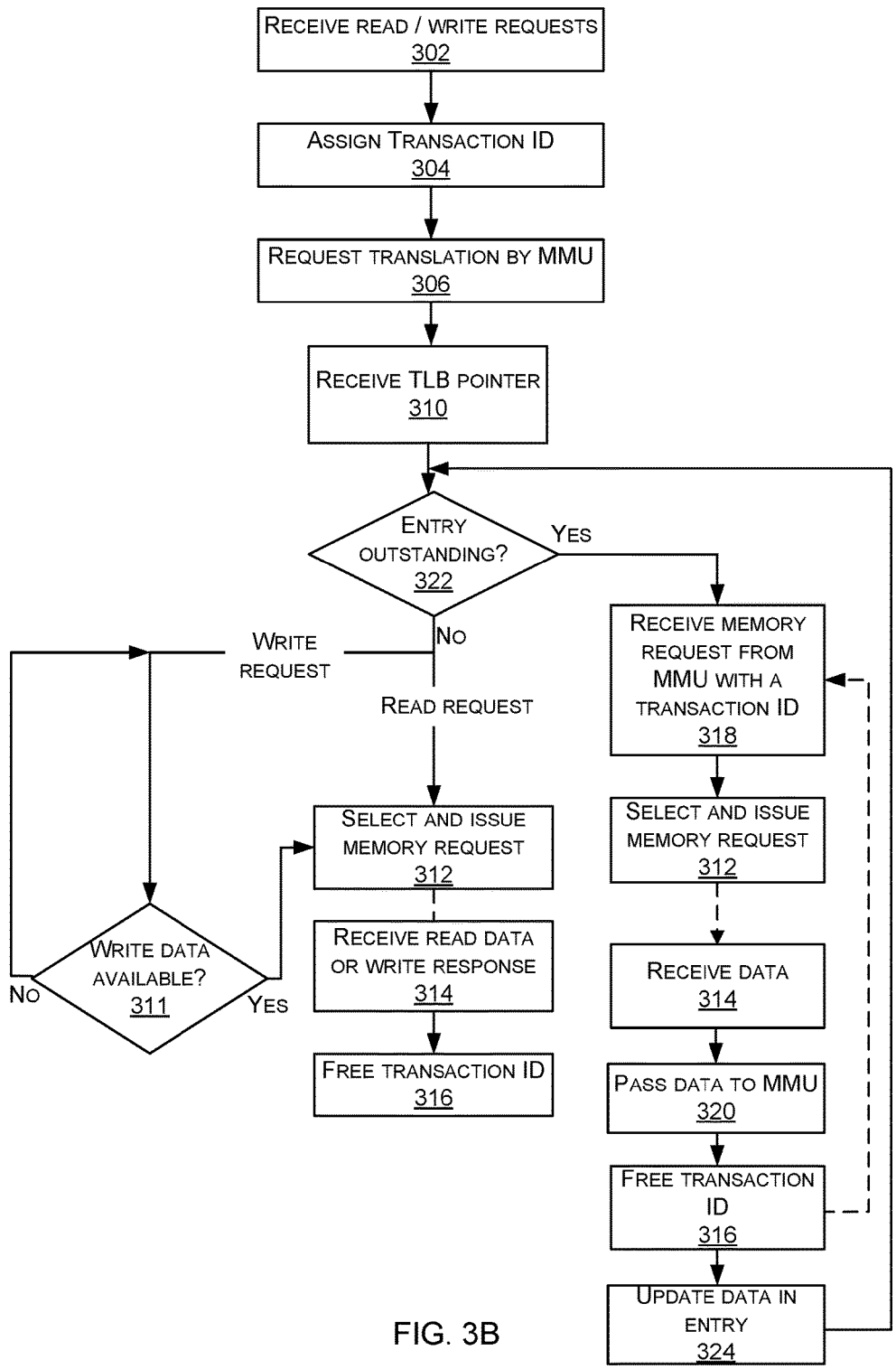
FIG. 3B is a flow diagram showing a second example method of operation of a converter module as described herein.
Figure 4:
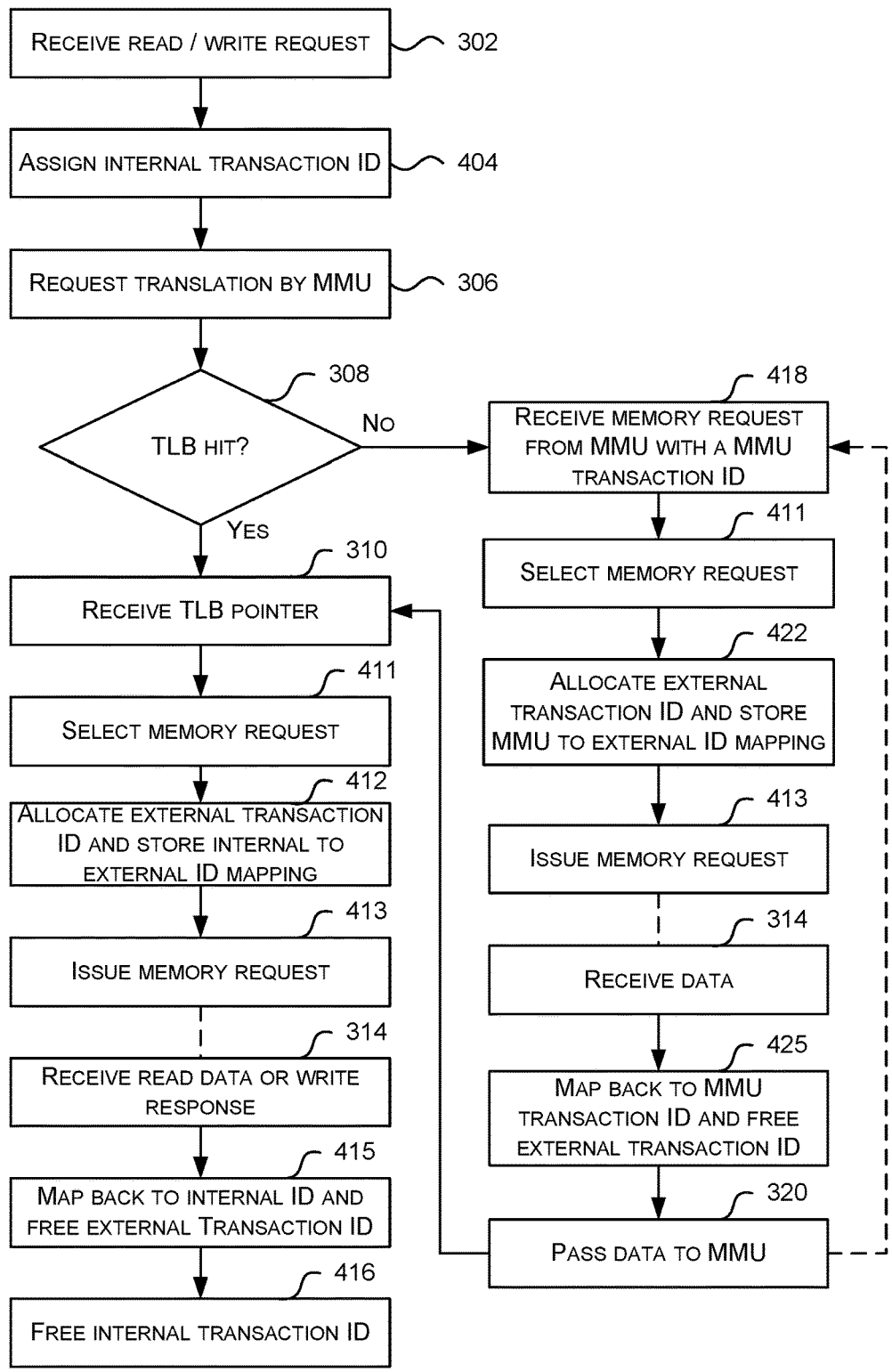
FIG. 4 is a flow diagram showing a third example method of operation of a converter module as described herein.

The operation of the converter module 202 and its component parts can be described in more detail with reference to FIGS. 3A, 3B and 4. FIGS. 3A, 3B and 4 show three different example methods of operation of the converter module 202; however, as can be seen from the diagrams, the methods have a number of method blocks in common.

In the method shown in FIGS. 3A and 3B, the converter module 202 receives a read/write request from the cache 204 (block 302) and a transaction ID is assigned by the assignment module 212 (block 304). The transaction ID which is assigned (in block 304) may be selected from a pool of available transaction IDs and the transaction IDs may be external transaction IDs, i.e. IDs which are used on the external bus 206. For example, where the external bus 206 uses the AXI 4 ACE protocol, the external transaction IDs which are assigned (in block 304) are AXI IDs.

Once a transaction ID has been assigned (in block 304), a translation is requested for any virtual memory addresses in the request (block 306). As described above, the translation request may be passed to the MMU 208 by the assignment module 212 (as shown by the arrow in FIG. 2) or by the transaction tracker module 214. The translation request includes the transaction ID which has been assigned to the incoming memory request (in block 304).

In the event of a TLB hit ('Yes' in block 308) the transaction tracker module 214 receives the translation from the MMU or a pointer to the translation in the TLB along with the transaction ID to which the translation relates (block 310). This enables the transaction tracker module 214, which tracks the status of each pending transaction, to update the status of the identified transaction to show that the translation is ready. For write requests, a transaction is only ready if the translation is available and the write data is also available i.e. stored in the OWDB ('Yes' in block 311). Once the memory request (identified by the transaction ID) is ready to be issued, the memory request, including the physical address which was obtained from the TLB (e.g. instead of the virtual memory address which was in the original incoming memory request), may be passed to the arbiter module 216.

The arbiter module 216 selects a memory request from those which are ready and issues it onto the external bus 206 (block 312) using the transaction ID that was previously assigned (in block 304). As described above, the selection (in block 312) may be performed based on one or more rules.

Subsequent to issuing a memory request with a particular transaction ID (in block 312), the arbiter module 216 receives read data (for a read request) or a write response (for a write request) with a matching transaction ID (block 314). Based on the transaction ID, the arbiter module 216 can determine if the memory request to which the read data or write response corresponds originated from the cache 204 or the MMU 208 and then forward the read data or write response to the transaction tracker module 214 (for cache originating requests) or the MMU 208 (for MMU originating requests).

Once the read/write request is complete (i.e. a response has been received from the external bus which effectively completes the lifecycle of that transaction), the transaction ID which was allocated to the request (in block 304) can be freed (block 316). This means that the transaction ID returns to the pool of available transaction IDs which can be allocated to an incoming request (in block 304).

In the event of a TLB miss ('No' in block 308) the transaction tracker module 214 may not immediately receive the translation or a translation pointer from the MMU 208, as shown in FIG. 3A. Instead, the MMU issues a memory request which is allocated a transaction ID within the MMU. The transaction ID which is allocated by the MMU may be selected from a separate pool of available external transaction IDs which are used only for MMU originating requests. The arbiter module 216 receives the memory request generated by the MMU along with its transaction ID (block 318) and the memory request is available for selection and issuance (in block 312) as described above. As also described above, MMU requests (as identified by their special transaction IDs) may be prioritized over cache originating requests in order to minimize the latency associated with the MMU/TLB miss.

Subsequently to issuing the MMU request (in block 312), the arbiter module 216 receives the data (in block 314) and can identify from the transaction ID that it relates to a memory request which was generated by the MMU 208. The arbiter module 216 therefore passes the data to the MMU (block 320) and the special MMU transaction ID is freed (block 316) by the arbiter module 216 or the MMU 208. As described above, a single TLB miss may require multiple memory look-ups (e.g. in the case of nested translations) and so the arbiter module may receive further memory requests (as indicated by the dotted arrow from block 316 to block 318) before the translation is available in the MMU for the cache originating request.

Once the translation is available, the transaction tracker module 214 receives the translation from the MMU or a pointer to the translation in the TLB along with the transaction ID to which the translation relates (block 310). As the translation is now ready, the memory request (identified by the transaction ID) is ready to be issued and so may be passed to the arbiter module 216. As noted above, for a write request, the write data must also be available (i.e. be stored in the OWDB) for the memory request to be ready to be issued ('Yes' in block 311). There is no similar constraint for read requests.

The arbiter module 216 selects a memory request from those which are ready (e.g. based on one or more rules) and issues it onto the external bus 206 (block 312) using the transaction ID that was previously assigned (in block 304).

Subsequent to issuing a memory request with a particular transaction ID (in block 312), the arbiter module 216 receives read data (for a read request) or a write response (for a write request) with a matching transaction ID. Based on the transaction ID, the arbiter module 216 can determine if the memory request to which the read data or write response corresponds originated from the cache 204 or the MMU 208 and then forward the read data or write response to the transaction tracker module 214 (for cache originating requests) or the MMU 208 (for MMU originating requests).

As described above, once the read/write request is complete, the transaction ID which was allocated to the cache originating request (in block 304) can be freed (block 316). This means that the transaction ID returns to the pool of available transaction IDs which can be allocated to another incoming request from the cache (in block 304).

FIG. 3B shows a variation on the method shown in FIG. 3A and described above. In this example method, irrespective of whether there is a TLB hit or miss, the transaction tracker module 214 receives a translation or a translation pointer from the MMU 208 (block 310); however in the event of a TLB miss, the pointer points to an entry which is marked as outstanding ('Yes' in block 322) and so the transaction tracker module 214 knows that the transaction is not yet ready. As described above, in the event of a TLB miss (which means that the entry is marked as outstanding, 'Yes' in block 322), the MMU issues a memory request which is allocated a transaction ID within the MMU (as described above with reference to FIG. 3A). The transaction ID which is allocated by the MMU may be selected from a separate pool of available external transaction IDs which are used only for MMU originating requests. The arbiter module 216 receives the memory request generated by the MMU along with its transaction ID (block 318) and the memory request is available for selection and issuance (in block 312) as described above. As also described above, MMU requests (as identified by their special transaction IDs) may be prioritized over cache originating requests in order to minimize the latency associated with the MMU/TLB miss.

Subsequently to issuing the MMU request (in block 312), the arbiter module 216 receives the data (in block 314) and can identify from the transaction ID that it relates to a memory request which was generated by the MMU 208. The arbiter module 216 therefore passes the data to the MMU (block 320) and the special MMU transaction ID is freed (block 316) by the arbiter module 216 or the MMU 208. As described above, a single TLB miss may require multiple memory look-ups (e.g. in the case of nested translations) and so the arbiter module may receive further memory requests (as indicated by the dotted arrow from block 316 to block 318) before the translation is available in the MMU (as updated in block 324) for the cache originating request.

Once the translation is available, the entry to which the pointer points is no longer marked as outstanding ('No' in block 322) and the memory request (identified by the transaction ID) is ready to be issued and so may be passed to the arbiter module 216. As noted above, for a write request, the write data must also be available (i.e. be stored in the OWDB) for the memory request to be ready to be issued ('Yes' in block 311). There is no similar constraint for read requests.

The arbiter module 216 selects a memory request from those which are ready (e.g. based on one or more rules) and issues it onto the external bus 206 (block 312) using the transaction ID that was previously assigned (in block 304).

Subsequent to issuing a memory request with a particular transaction ID (in block 312), the arbiter module 216 receives read data (for a read request) or a write response (for a write request) with a matching transaction ID. Based on the transaction ID, the arbiter module 216 can determine if the memory request to which the read data or write response corresponds originated from the cache 204 or the MMU 208 and then forward the read data or write response to the transaction tracker module 214 (for cache originating requests) or the MMU 208 (for MMU originating requests).

As described above, once the read/write request is complete, the transaction ID which was allocated to the cache originating request (in block 304) can be freed (block 316). This means that the transaction ID returns to the pool of available transaction IDs which can be allocated to another incoming request from the cache (in block 304).

By using the methods described above and shown in FIGS. 3A and 3B, the latency resulting from MMU misses can be hidden and out-of-order translation of addresses can be supported. The methods improve performance, latency toleration and bus utilization.

In contrast to the method shown in FIGS. 3A and 3B, in the method shown in FIG. 4, three types of transaction IDs are used: internal transaction IDs, MMU transaction IDs (which may be considered to be a special type of the internal transaction IDs) and external transaction IDs. Unlike the method of FIGS. 3A and 3B, in the method of FIG. 4, the assignment module 212 assigns internal transaction IDs to incoming memory requests and the MMU 208 assigns MMU transaction IDs to any memory requests it generates. These transaction IDs are then mapped to external transaction IDs by the arbiter module 216 before memory requests are issued onto the external bus.

By using internal transaction IDs in this way, it is possible to use a smaller number of external transaction IDs because it is not necessary to reserve a number of external transaction IDs for MMU requests. This makes a more flexible system (e.g. the external bus does not need to support N requests from the cache plus M requests from the MMU but instead a fixed size pool of external transaction IDs can be used by whatever proportion of MMU and cache requests happen to be in-flight at any one point in time). The total number of internal transaction IDs, including MMU transaction IDs may be chosen to match the total number of external transaction IDs, or there may be more internal transaction IDs than external transaction IDs.

Where there are more internal transaction IDs (including the MMU transaction IDs) than external IDs, it may not be possible to issue all the memory requests which are ready because there may not be any available external transaction IDs and so memory requests may be buffered within the arbiter module 216 and/or the transaction tracker module 214.

If the number of internal transaction IDs, not including the MMU transaction IDs, is increased then the size of the memory in the transaction tracker module 214 which is used to track all the pending transactions gets larger; however, the efficiency of the memory hierarchy improves.

In the method shown in FIG. 4, the converter module 202 receives a read/write request from the cache 204 (block 302) and an internal transaction ID is assigned by the assignment module 212 (block 404). The internal transaction ID which is assigned (in block 404) may be selected from a pool of available internal transaction IDs.

Once an internal transaction ID has been assigned (in block 404), a translation is requested for any virtual memory addresses in the request (block 306). As described above, the translation request may be passed to the MMU 208 by the assignment module 212 (as shown by the arrow in FIG. 2) or by the transaction tracker module 214. The translation request includes the internal transaction ID which has been assigned to the incoming memory request (in block 404).

In the event of a TLB hit ('Yes' in block 308) the transaction tracker module 214 receives the translation from the MMU or a pointer to the translation in the TLB along with the internal transaction ID to which the translation relates (block 310). This enables the transaction tracker module 214, which tracks the status of each pending transaction, to update the status of the identified transaction to show that the translation is ready. Once the memory request (identified by the internal transaction ID), including the physical address which was obtained from the TLB (e.g. instead of the virtual memory address which was in the incoming memory request), is ready to be issued it may be passed to the arbiter module 216.

The arbiter module 216 selects a memory request from those which are ready (block 411) where, as described above, this selection may be based on one or more rules. Before the memory request can be issued (block 413), it must first be allocated an external transaction ID from a pool of available external transaction IDs and the mapping between the internal transaction ID and the external transaction ID is stored in the arbiter module 216 (block 412).

In an example, the external transaction ID may be allocated by remapping logic within the arbiter module 216 which retains an array of which internal transaction ID has been assigned to each external transaction ID. When a request has been selected by the arbiter module 216 (in block 411), the remapping logic finds an available free entry in the array (e.g. the first available free entry in the array). The internal transaction ID is stored in the identified array entry and the entry number which has been assigned then forms the external transaction ID which is output onto the external bus 206 (in block 413).

Subsequent to issuing a memory request with a particular external transaction ID (in block 413), the arbiter module 216 receives read data (for a read request) or a write response (for a write request) with a matching external transaction ID (block 314). The external transaction ID is then mapped back to the internal ID and the external transaction ID is freed (block 415).

In an example where the array described above is used, the received external transaction ID is used as the index into the remapping array and this allows the original internal transaction ID to be obtained. Once this occurs, the entry is marked as empty again, allowing the entry (and hence the external transaction ID) to be reallocated to a new request.

Based on the internal transaction ID, the arbiter module 216 can determine if the memory request to which the read data or write response corresponds originated from the cache 204 or the MMU 208 and then forward the read data or write response to the transaction tracker module 214 (for cache originating requests) or the MMU 208 (for MMU originating requests). For example, a first range or type of IDs may be used as internal transaction IDs for cache originating request and a second, different, range or type of IDs may be used as MMU transaction IDs.

Once the read/write request is complete, the internal transaction ID which was allocated to the request (in block 404) can be freed (block 416). This means that the internal transaction ID returns to the pool of available internal transaction IDs which can be allocated to an incoming request (in block 404).

In the event of a TLB miss ('No' in block 308) the transaction tracker module 214 may not immediately receive the translation or a translation pointer from the MMU 208; alternatively, as described above with reference to FIG. 3B, a translation pointer may be received which points to an entry which is marked as outstanding. In the event of a TLB miss the MMU issues a memory request which is allocated a MMU transaction ID within the MMU. The MMU transaction ID which is allocated by the MMU may be selected from a pool of available MMU transaction IDs. The arbiter module 216 receives the memory request generated by the MMU along with its MMU transaction ID (block 418) and is available for selection (in block 411) and issuance (in block 413). MMU requests (as identified by their MMU transaction IDs) may be prioritized (when selecting a request in block 411) over cache originating requests in order to minimize the latency associated with the MMU/TLB miss.

Prior to issuing the memory request (in block 413), an external transaction ID is allocated and the MMU to external ID mapping is stored (block 422). The external transaction ID may be allocated from the pool of available external transaction IDs and unlike the method described above with reference to FIGS. 3A and 3B, the same pool of external transaction IDs may be used for both cache originating and MMU originating memory requests.

In an example, the external transaction ID may be allocated by the remapping logic (described above). When a request has been selected by the arbiter module 216 (in block 411), the remapping logic finds an available free entry in the array. The MMU transaction ID is stored in this particular array entry and the entry number which has been assigned then forms the external transaction ID which is output onto the external bus 206 (in block 413).

Subsequently to issuing the MMU request (in block 413), the arbiter module 216 receives the data (in block 314) along with the external transaction ID. This external transaction ID is then mapped back to the internal ID, which in this case is a MMU transaction ID (e.g. using the array maintained by the remapping logic), and the external transaction ID is freed (block 425).

The arbiter module 216 can identify from the MMU transaction ID that the data received (in block 314) relates to a memory request which was generated by the MMU 208. The arbiter module 216 therefore passes the data to the MMU (block 320) and the MMU transaction ID is freed by the MMU 208. As described above, a single TLB miss may require multiple memory look-ups (e.g. in the case of nested translations) and so the arbiter module may receive further memory requests (as indicated by the dotted arrow from block 320 to block 418) before the translation is available in the MMU for the cache originating request.

Once the translation is available, the transaction tracker module 214 receives the translation from the MMU or a pointer to the translation in the TLB along with the transaction ID to which the translation relates (block 310). As the translation is now ready, the memory request (identified by the internal transaction ID allocated in block 404) is ready to be issued and so may be passed to the arbiter module 216. As noted above, for write requests, the write data must also be available in order that a write request is ready to be issued (e.g. the write data is stored in the OWDB).

The arbiter module 216 selects a memory request from those which are ready (block 411), allocates an external transaction ID and stores the internal to external transaction ID mapping (block 412) and issues it onto the external bus 206 (block 413) using the external transaction ID.

Subsequent to issuing a memory request with a particular external transaction ID (in block 413), the arbiter module 216 receives read data (for a read request) or a write response (for a write request) with a matching external transaction ID (block 314). The arbiter module 216 (e.g. the remapping logic, described above) maps the external transaction ID back to the internal transaction ID and frees the external transaction ID (block 415). Based on the internal transaction ID, the arbiter module 216 can determine that in this case the memory request originated from the cache 204 and then forward the read data or write response to the transaction tracker module 214.

As described above, once the read/write request is complete, the internal transaction ID which was allocated to the cache originating request (in block 404) can be freed (block 416). This means that the internal transaction ID returns to the pool of available internal transaction IDs which can be allocated to another incoming request from the cache (in block 404).

In the examples described above with reference to FIGS. 2-4, read and write requests from the cache are handled together (i.e. treated in the same way and without distinguishing between read and write requests such that transaction IDs for read and write requests are allocated from the same pool) and the MMU requests are handled separately, with transaction IDs for MMU requests being allocated from a separate pool (where these transaction IDs may be internal IDs as in the example shown in FIG. 4 or external IDs as in the example shown in FIGS. 3A and 3B). In other examples, however, read and write requests may be handled separately, such that transaction IDs for read requests are allocated from a separate pool of IDs to the transaction IDs for write requests. As with the earlier examples, the transaction IDs which are allocated may be external IDs (as described with reference to FIG. 6 below) or internal IDs (as described with reference to FIG. 7 below).

By allocating transaction IDs for read and write requests separately, the memory hierarchy can be better matched to the external bus, particularly if the bus and/or the off-chip memory (e.g. main memory 108 in the hierarchy shown in FIG. 1) can support different numbers of reads and writes (e.g. more reads than writes) within a fixed time window. Additionally reads cannot become stuck behind writes (e.g. where the external bus has separate channels for reads and writes).

Figure 5:
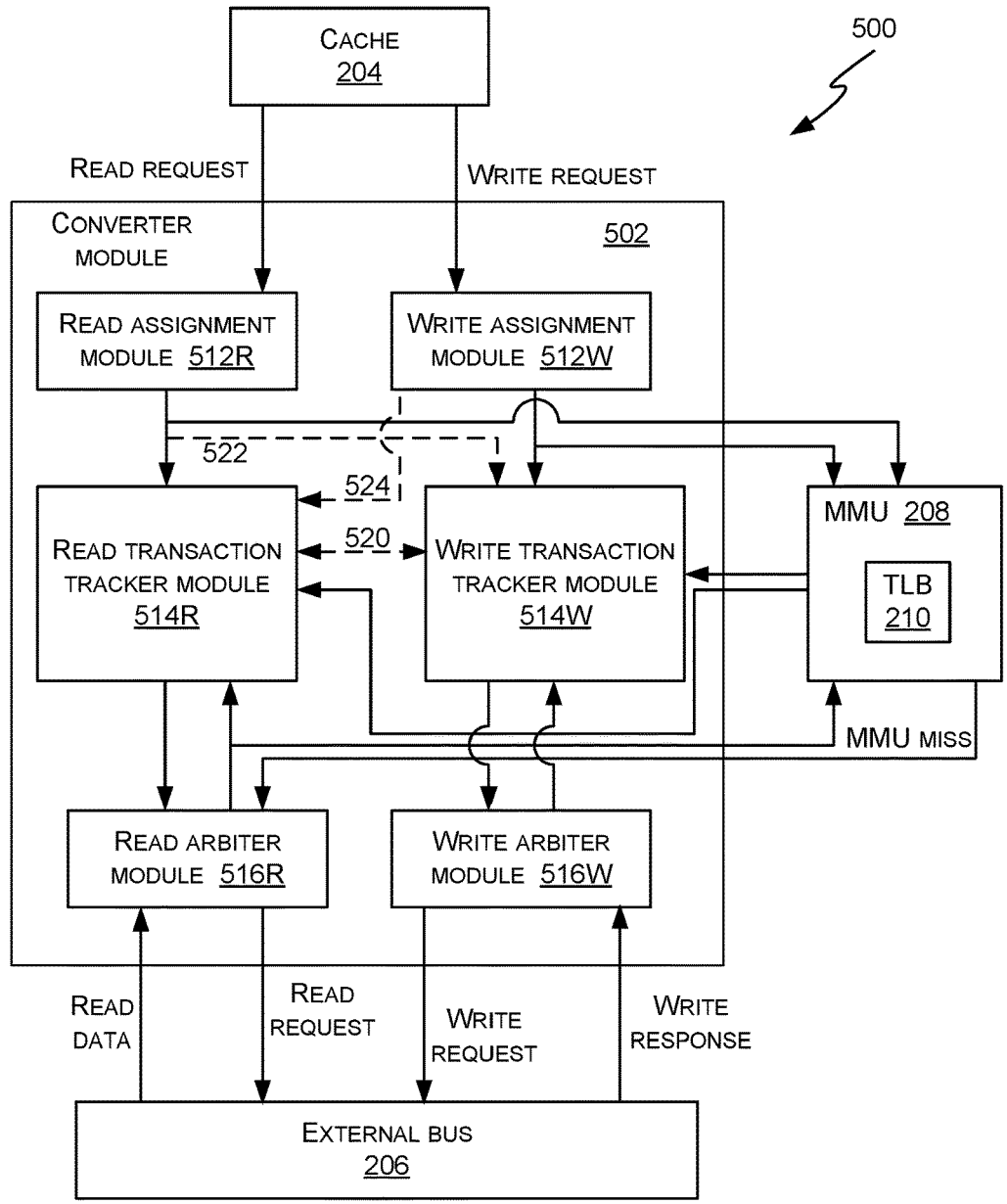
FIG. 5 is a schematic diagram of part of a memory hierarchy including a second example converter module.

FIG. 5 is a schematic diagram 500 of part of a memory hierarchy including a converter module 502 which receives memory requests from an on-chip cache 204 which is the furthest from the processor (i.e. the last on-chip cache in the hierarchy e.g. an L2 cache) and issues memory requests to the next memory in the hierarchy (e.g. the main memory 108 in the example of FIG. 1) via an external bus 206 (to which the off-chip memory is connected). The converter module 502 is connected to a MMU 208 which comprises a TLB 210.

Compared to the converter module 202 shown in FIG. 2, it can be seen that the converter module 502 shown in FIG. 5 comprises two parallel paths, one for read requests (on the left of the diagram) and one for write requests (on the right of the diagram). Each path (read/write) comprises an assignment module 512R, 512W, a transaction tracker module 514R, 514W and an arbiter module 516R, 516W. As with FIG. 2, the OWDB is not shown in FIG. 5.

The read assignment module 512R receives the read requests from the cache 204 and assigns transaction IDs to those read requests and the write assignment module 512W receives the write requests from the cache 204 and assigns transaction IDs to those write requests. The read transaction tracker module 514R tracks each incoming read request using the transaction ID assigned by the read assignment module 512R (e.g. to determine whether the translation is available in the TLB and so whether the request can be issued) and the write transaction tracker module 514W tracks each incoming write request using the transaction ID assigned by the write assignment module 512W.

The read assignment module 512R or the read transaction tracker module 514R may send a translation request to the MMU 208 for each memory read request received from the cache 204. These translation requests are tagged with the transaction ID of the corresponding memory read request. In response to a translation request, the MMU 208 returns the translation or a pointer to the translation to the read transaction tracker module 514R along with the transaction ID (so that the read transaction tracker module 514R can match up translations/translation pointers and corresponding memory read requests).

Similarly, the write assignment module 512W or the write transaction tracker module 514W may send a translation request to the MMU 208 for each memory write request received from the cache 204. These translation requests are tagged with the transaction ID of the corresponding memory write request. In response to a translation request, the MMU 208 returns the translation or a pointer to the translation to the write transaction tracker module 514W along with the transaction ID (so that the read transaction tracker module 514W can match up translations or translation pointers and corresponding memory write requests).

In the event of a MMU hit, the translation or translation pointer can be returned straight away to the respective transaction tracker module 514R, 514W (i.e. to the read transaction tracker module 514R for translations relating to a memory read request and to the write transaction tracker module 514W for translations relating to a memory write request).

In the event of a MMU/TLB miss (i.e. where a translation is not stored in the TLB 210) the MMU generates a memory read request and waits for the data to be returned before it can return the translation or translation pointer for the particular transaction ID. If the MMU uses nested translations, it may be necessary to make several calls to memory (i.e. to issue several memory read requests) before the translation/translation pointer can be returned to the transaction tracker module 514R, 514W and this results in several cycles of latency.

The read arbiter module 516R receives memory read requests which are ready to be issued from the read transaction tracker module 514R and also receives memory read requests from the MMU 208 which are generated in response to a MMU/TLB miss. The read requests that are received from the read transaction tracker module 514R originate from the cache 202 but now include the physical address which was obtained from the TLB (instead of the virtual memory address). The read arbiter module 516R selects one or more of the memory read requests it receives and issues them onto the external bus 206 (e.g. one per clock cycle). The read arbiter module 516R uses one or more rules to determine which memory read request to select and issue at any time, rather than working in transaction ID order. In the event that more memory read requests are ready to be issued than can be issued onto the external bus 206, those memory read requests which are waiting to be issued may be buffered within the read arbiter module 516R.

In various examples the read arbiter module 516R may prioritise memory read requests that were generated by the MMU 208 (as a consequence of a MMU/TLB miss) over memory read requests that were generated by the cache 204. If there are no memory read requests that were generated by the MMU 208, the memory read requests generated by the cache 204 may be selected in order of MMU hits (i.e. in the order that the translations in TLB are available), however, the read arbiter module 516R may also attempt to issue memory read requests from the cache 204 in age order wherever possible (e.g. if there are two memory read requests from the cache where the translation is available, the oldest one may be selected to be issued onto the external bus 206).

The read arbiter module 516R also receives read data back from the external bus 206 and the read data may be received back in an order which is different to the order in which the memory read requests were issued onto the external bus 206 by the read arbiter module 516R. However, the read data which is received is accompanied by the corresponding transaction ID and so the read arbiter module 516R can determine whether the read data corresponds to a request issued by the cache 204 or by the MMU 208. Where the read data corresponds to a request issued by the MMU 208, the read data is passed to the MMU 208. Where the read data corresponds to a read request issued by the cache 204, the read data is passed to the read transaction tracker module 514R and then on to the cache.

The write arbiter module 516W receives memory write requests which are ready to be issued from the write transaction tracker module 514W and as described above, for a write request to be ready to be issued, the write data must also be available (e.g. stored in the OWDB). The write requests that are received from the write transaction tracker module 514W originate from the cache 202 but now include the physical address which was obtained from the TLB (instead of the virtual memory address). The write arbiter module 516W selects one or more of the memory write requests it receives and issues them onto the external bus 206 (e.g. one per clock cycle in implementations with a separate data bus or data channel). The write arbiter module 516W uses one or more rules to determine which memory write request to select and issue at any time, rather than working in transaction ID order. In the event that more memory write requests are ready to be issued than can be issued onto the external bus 206, those memory write requests which are waiting to be issued may be buffered within the write arbiter module 516W.

In various examples, the memory write requests generated by the cache 204 may be selected in order of MMU hits (i.e. in the order that the translations in TLB are available), however, the write arbiter module 516W may also attempt to issue memory write requests from the cache 204 in age order wherever possible (e.g. if there are two memory write requests from the cache where the translation is available, the oldest one may be selected to be issued onto the external bus 206).

The write arbiter module 516W also receives write responses (e.g. confirmation that the write has been written) back from the external bus 206 and the write responses may be received back in an order which is different to the order in which the memory write requests were issued onto the external bus 206 by the write arbiter module 516W. However, the write responses which are received are accompanied by the corresponding transaction ID. The write responses are passed to the write transaction tracker module 514W.

The operation of the converter module 502 and its component parts can be described in more detail with reference to FIGS. 3A, 3B and 4. FIGS. 3A, 3B and 4 show two different example methods of operation of the converter module 502, with each of the methods being replicated for the separate read and write paths; however, as can be seen from the diagrams, the methods have a number of method blocks in common.

In the method shown in FIGS. 3A and 3B, the converter module 502 receives a read/write request from the cache 204 (block 302) and read requests are handled by the read path (comprising the read assignment module 512R, read transaction tracker module 514R and read arbiter module 516R) and write requests are handled by the separate write path (comprising the write assignment module 512W, write transaction tracker module 514W and write arbiter module 516W).

If the request is a read request, a transaction ID is assigned by the read assignment module 512R and if the request is a write request, a transaction ID is assigned by the write assignment module 512W (block 304). The transaction ID which is assigned (in block 304) may be selected from a pool of available transaction IDs and the transaction IDs may be external transaction IDs, i.e. IDs which are used on the external bus 206. For example, where the external bus 206 uses the AXI 4 ACE protocol, the external transaction IDs which are assigned (in block 304) are AXI IDs. Separate pools of available transaction IDs are used by the read and write assignment modules 512R, 512W, such that read requests are assigned transaction IDs from a first pool of available transaction IDs and write requests are assigned transaction IDs from a second pool of available transaction IDs.

Once a transaction ID has been assigned (in block 304), a translation is requested for any virtual memory addresses in the request (block 306). The translation request for a read request may be passed to the MMU 208 by the read assignment module 512R (as shown by the arrow in FIG. 5) or by the read transaction tracker module 514R. The translation request for a write request may be passed to the MMU 208 by the write assignment module 512W (as shown by the arrow in FIG. 5) or by the write transaction tracker module 514W. Irrespective of whether the translation request relates to a read or write, the translation request includes the transaction ID which has been assigned to the incoming memory request (in block 304).

In the event of a TLB hit ('Yes' in block 308) for a translation request which corresponds to a read request the read transaction tracker module 514R receives the translation from the MMU or a pointer to the translation in the TLB along with the transaction ID to which the translation relates (block 310). This enables the read transaction tracker module 514R, which tracks the status of each pending read transaction, to update the status of the identified transaction to show that the translation is ready. Once the translation is ready, the memory read request (identified by the transaction ID) is ready to be issued and so the memory read request, including the physical address which was obtained from the TLB (instead of the virtual memory address), may be passed to the read arbiter module 516R.

Similarly, in the event of a TLB hit ('Yes' in block 308) for a translation request which corresponds to a write request the write transaction tracker module 514W receives the translation from the MMU or a pointer to the translation in the TLB along with the transaction ID to which the translation relates (block 310). This enables the write transaction tracker module 514W, which tracks the status of each pending write transaction, to update the status of the identified transaction to show that the translation is ready. Once the translation is ready, the memory write request (identified by the transaction ID) is ready to be issued and so the memory write request, including the physical address which was obtained from the TLB (instead of the virtual memory address), may be passed to the write arbiter module 516W.

The read arbiter module 516R selects a memory read request from those which are ready and issues it onto the external bus 206 (block 312) using the transaction ID that was previously assigned (in block 304). Similarly, the write arbiter module 516R selects a memory write request from those which are ready and issues it onto the external bus 206 (block 312) using the transaction ID that was previously assigned (in block 304). As described above, the selection (in block 312) may be based on one or more rules and different rules may be used by the read arbiter module 516R and the write arbiter module 516W (e.g. because the write arbiter module 516W does not issue memory requests generated by the MMU 208).

Subsequent to issuing a memory read request with a particular transaction ID (in block 312), the read arbiter module 516R receives read data with a matching transaction ID (block 314). Based on the transaction ID, the read arbiter module 516R can determine if the memory request originated from the cache 204 or the MMU 208 and then forward the read data to the read transaction tracker module 514R (for cache originating requests) or the MMU 208 (for MMU originating requests).

Subsequent to issuing a memory write request with a particular transaction ID (in block 312), the write arbiter module 516W receives a write response with a matching transaction ID (block 314). The write arbiter module 516W forwards the write response to the write transaction tracker module 514W.

Once a read request is complete, the transaction ID which was allocated to the read request (in block 304) can be freed (block 316). This means that the transaction ID returns to the pool of available transaction IDs for read requests which can be allocated to an incoming read request (in block 304).

Once a write request is complete, the transaction ID which was allocated to the write request (in block 304) can be freed (block 316). This means that the transaction ID returns to the pool of available transaction IDs for write requests which can be allocated to an incoming write request (in block 304).

In the event of a TLB miss ('No' in block 308) for a translation request which corresponds to a read request the read transaction tracker module 514R may not immediately receive the translation or a translation pointer from the MMU 208 (as shown in FIG. 3A). Alternatively, as described above with reference to FIG. 3B, a translation pointer may be received which points to an entry which is marked as outstanding. Similarly, in the event of a TLB miss ('No' in block 308) for a translation request which corresponds to a write request the write transaction tracker module 514W may not immediately receive the translation or a translation pointer from the MMU 208 (as shown in FIG. 3A). Alternatively, as described above with reference to FIG. 3B, a translation pointer may be received which points to an entry which is marked as outstanding.

In the event of a TLB miss (for misses relating to read or write requests and as described above with reference to both FIG. 3A and FIG. 3B), the MMU issues a memory read request which is allocated a transaction ID within the MMU. The transaction ID which is allocated by the MMU may be selected from a separate pool of available external transaction IDs which are used only for MMU originating requests. The read arbiter module 516R receives the memory read request generated by the MMU along with its transaction ID (block 318) and is available for selection and issuance (in block 312) by the read arbiter module 516R as described above. As also described above, MMU read requests (as identified by their special transaction IDs) may be prioritized (by the read arbiter module 516R) over cache originating read requests in order to minimize the latency associated with the MMU/TLB miss.

Subsequently to issuing the MMU request (in block 312), the read arbiter module 516R receives the data (in block 314) and can identify from the transaction ID that it relates to a memory read request which was generated by the MMU 208. The read arbiter module 516R therefore passes the data to the MMU (block 320) and the special MMU transaction ID is freed (block 316) by the read arbiter module 516R or the MMU 208. As described above, a single TLB miss may require multiple memory look-ups (e.g. in the case of nested translations) and so the read arbiter module 516R may receive further memory read requests (as indicated by the dotted arrow from block 316 to block 318) before the translation is available in the MMU for the cache originating read or write request.

Once the translation is available for a translation request which corresponds to a read request, the read transaction tracker module 514R receives the translation from the MMU or a pointer to the translation in the TLB along with the transaction ID to which the translation relates (block 310) or in the alternative example, as shown in FIG. 3B, the entry to which the pointer points is no longer outstanding. As the translation is now ready, the memory read request (identified by the transaction ID) is ready to be issued and so may be passed to the read arbiter module 516R.

Similarly, once the translation is available for a translation request which corresponds to a write request, the write transaction tracker module 514W receives the translation from the MMU or a pointer to the translation in the TLB along with the transaction ID to which the translation relates (block 310) or in the alternative example, as shown in FIG. 3B, the entry to which the pointer points is no longer outstanding. As the translation is now ready, the memory write request (identified by the transaction ID) is ready to be issued and so may be passed to the write arbiter module 516W.

As described above, the read arbiter module 516R selects a memory read request from those which are ready (e.g. based on one or more rules) and issues it onto the external bus 206 (block 312) using the transaction ID that was previously assigned (in block 304). Similarly (although using different rules to perform the selection in some examples) the write arbiter module 516W selects a memory write request from those which are ready and issues it onto the external bus 206 (block 312) using the transaction ID that was previously assigned (in block 304).

Subsequent to issuing a memory read request with a particular transaction ID (in block 312), the read arbiter module 516R receives read data with a matching transaction ID. Based on the transaction ID, the read arbiter module 516R can determine if the memory request originated from the cache 204 or the MMU 208 and then forward the read data to the read transaction tracker module 514R (for cache originating requests) or the MMU 208 (for MMU originating requests).

Subsequent to issuing a memory write request with a particular transaction ID (in block 312), the write arbiter module 516W receives a write response with a matching transaction ID and forwards the write response to the write transaction tracker module 514W.

As described above, once a read request is complete, the transaction ID which was allocated to the cache originating request (in block 304) can be freed (block 316). This means that the transaction ID returns to the pool of available transaction IDs for read requests which can be allocated to another incoming read request from the cache (in block 304). Similarly, once a write request is complete, the transaction ID which was allocated to the cache originating request (in block 304) can be freed (block 316). This means that the transaction ID returns to the pool of available transaction IDs for write requests which can be allocated to another incoming write request from the cache (in block 304).

In the method shown in FIGS. 3A and 3B, external transaction IDs are used and when used in the memory hierarchy 500 shown in FIG. 5, these external transaction IDs are allocated from a number of separate pools of IDs, e.g. one pool for read requests, another for write requests and a further pool for MMU requests (which are a special case of read requests and so are handled by the read path). It will be appreciated that in various examples, there may be other pools of transaction IDs which are used for other types of memory requests and which may be handled by separate paths within the converter module 502 (e.g. a separate path which provides the write data corresponding to a write request).

In contrast, in the method shown in FIG. 4 both internal and external transaction IDs are used, with the external transaction IDs only being assigned when a read/write request is ready to be issued onto the external bus. When used in the memory hierarchy 500 shown in FIG. 5, the method of FIG. 4 uses four types of transaction IDs: internal read transaction IDs, internal write transaction IDs, MMU transaction IDs (which may be considered to be a special type of internal read transaction IDs) and external transaction IDs. Unlike the method of FIGS. 3A and 3B, in the method of FIG. 4, the read and write assignment modules 512R, 512W assign internal transaction IDs (i.e. the read assignment module 512R assigns internal read transaction IDs and the write assignment module 512W assigns internal write transaction IDs) and the MMU 208 assigns MMU transaction IDs to any memory requests it generates. These internal transaction IDs are then mapped to external transaction IDs by the read or write arbiter module 516R, 516W before memory requests are issued onto the external bus. There may be separate pools for external transaction IDs for reads and writes or there may be a single set of external transaction IDs which is used for both read and write requests.

By using internal transaction IDs in this way, it is possible to use a smaller number of external transaction IDs because it is not necessary to reserve a number of external transaction IDs for MMU requests. As described above, this makes a more flexible system (e.g. the external bus does not need to support N requests from the cache plus M requests from the MMU but instead a fixed size pool of external transaction IDs can be used by whatever proportion of MMU and cache requests happen to be in-flight at any one point in time). The number of available read and write internal transaction IDs may be selected to match the capabilities of the external bus and/or off-chip memory. The total number of internal transaction IDs, including MMU transaction IDs may be chosen to match the total number of external transaction IDs, or there may be more internal transaction IDs than external transaction IDs.

Where there are more internal transaction IDs (including the MMU transaction IDs) than external IDs, it may not be possible to issue all the memory requests which are ready because there may not be any available external transaction IDs and so memory requests may be buffered within the read and/or write arbiter module 516R, 516W and/or the read and/or write transaction tracker module 514R, 514W.

If the number of internal read and/or write transaction IDs (not including the MMU transaction IDs), is increased then the size of the memory in the corresponding read/write transaction tracker module 514R, 514W which is used to track all the pending read or write transactions respectively gets larger; however, the efficiency of the memory hierarchy improves.

In the method shown in FIG. 4, when used with the memory hierarchy 500 shown in FIG. 5, when the converter module 502 receives a read request from the cache 204 (block 302), an internal read transaction ID is assigned from a pool of available internal read transaction IDs by the read assignment module 512R (block 404). Similarly, when the converter module 512 receives a write request from the cache 204 (block 302), an internal write transaction ID is assigned from a pool of available internal write transaction IDs by the write assignment module 512W (block 404).

Once an internal transaction ID has been assigned (in block 404), a translation is requested for any virtual memory addresses in the request (block 306). As described above, for a read request the translation request may be passed to the MMU 208 by the read assignment module 512R (as shown by the arrow in FIG. 2) or by the read transaction tracker module 514R. Similarly, for a write request the translation request may be passed to the MMU 208 by the write assignment module 512W (as shown by the arrow in FIG. 2) or by the write transaction tracker module 514W. The translation request which is passed to the MMU 208 includes the internal read/write transaction ID which has been assigned to the incoming memory request (in block 404).

In the event of a TLB hit ('Yes' in block 308) for a read request the read transaction tracker module 514R receives the translation from the MMU or a pointer to the translation in the TLB along with the internal read transaction ID to which the translation relates (block 310). This enables the read transaction tracker module 514R, which tracks the status of each pending read transaction, to update the status of the identified read transaction to show that the translation is ready. Once the translation is ready, the memory read request (identified by the internal read transaction ID), including the physical address which was obtained from the TLB (instead of the virtual memory address), is ready to be issued and so may be passed to the read arbiter module 516R.

In the event of a TLB hit ('Yes' in block 308) for a write request the write transaction tracker module 514W receives the translation from the MMU or a pointer to the translation in the TLB along with the internal write transaction ID to which the translation relates (block 310). This enables the write transaction tracker module 514W, which tracks the status of each pending write transaction, to update the status of the identified write transaction to show that the translation is ready. Once the translation is ready, the memory write request (identified by the internal write transaction ID), including the physical address which was obtained from the TLB (instead of the virtual memory address), is ready to be issued and so may be passed to the write arbiter module 516W.

The read arbiter module 516R selects a memory read request from those which are ready (block 411) where, as described above, this selection may be based on one or more rules. Before the memory read request can be issued (block 413), it must first be allocated an external transaction ID from a pool of available external transaction IDs and the mapping between the internal read transaction ID and the external transaction ID is stored in the read arbiter module 516R (block 412).

Similarly, the write arbiter module 516W selects a memory write request from those which are ready (block 411) where, as described above, this selection may be based on one or more rules and where the rules may be different for the read arbiter module 516R and the write arbiter module 516W. Before the memory write request can be issued (block 413), it must first be allocated an external transaction ID from a pool of available external transaction IDs (where, as described above, there may be separate pools of external write transaction IDs and external read transaction IDs, e.g. for an external bus with separate read/write channels) and the mapping between the internal write transaction ID and the external transaction ID is stored in the write arbiter module 516W (block 412).

In various example, the external transaction ID may be allocated by remapping logic in each of the arbiter modules 516R, 516W which retains an array of which internal read/write transaction ID has been assigned to each external transaction ID. When a request has been selected by an arbiter module 516R, 516W (in block 411), the remapping logic finds the first available free entry in the array (where each arbiter module maintains a separate array and uses a separate pool of external transaction IDs). The internal read/write transaction ID is stored in this particular array entry and the entry number which has been assigned then forms the external transaction ID which is output onto the external bus 206 (in block 413).

Subsequent to issuing a memory request with a particular external transaction ID (in block 413), the read arbiter module 516R receives read data with a matching external transaction ID (block 314). The external transaction ID is then mapped back to the internal read transaction ID and the external transaction ID is freed (block 415).

In an example where the array described above is used, the received external transaction ID is used as the index into the remapping array for read requests and this allows the original internal read transaction ID to be obtained. Once this occurs, the entry is marked as empty again, allowing the external transaction ID to be reallocated to a new read request.

Based on the internal read transaction ID, the read arbiter module 516R can determine if the memory read request originated from the cache 204 or the MMU 208 and then forward the read data to the read transaction tracker module 514R (for cache originating requests) or the MMU 208 (for MMU originating requests).

Once the read request is complete, the internal read transaction ID which was allocated to the request (in block 404) can be freed (block 416). This means that the internal read transaction ID returns to the pool of available internal read transaction IDs which can be allocated to an incoming read request (in block 404).

Subsequent to issuing a memory request with a particular external transaction ID (in block 413), the write arbiter module 516W receives a write response with a matching external transaction ID (block 314). The external transaction ID is then mapped back to the internal write transaction ID and the external transaction ID is freed (block 415).

In an example where the array described above is used, the received external transaction ID is used as the index into the remapping array for write requests and this allows the original internal write transaction ID to be obtained. Once this occurs, the entry is marked as empty again, allowing the external transaction ID to be reallocated to a new write request. Following the remapping, the write response is forwarded to the write transaction tracker module 514W.

Once the write request is complete, the internal write transaction ID which was allocated to the request (in block 404) can be freed (block 416). This means that the internal write transaction ID returns to the pool of available internal write transaction IDs which can be allocated to an incoming write request (in block 404).

In the event of a TLB miss ('No' in block 308), the read transaction tracker module 514R (for a read request) or write transaction tracker module 514W (for a write request) may not immediately receive the translation or a translation pointer from the MMU 208 (as described above with reference to FIG. 3A) or may receive a translation pointer which points to an entry which is marked as outstanding (as described above with reference to FIG. 3B). Instead, the MMU issues a memory read request which is allocated a MMU transaction ID within the MMU. The MMU transaction ID which is allocated by the MMU may be selected from a pool of available MMU transaction IDs. The read arbiter module 516R receives the memory read request generated by the MMU along with its MMU transaction ID (block 418) and is available for selection (in block 411) and issuance (in block 413). MMU read requests (as identified by their MMU transaction IDs) may be prioritized (when selecting a read request in block 411) over cache originating read requests in order to minimize the latency associated with the MMU/TLB miss.

Prior to issuing the memory read request (in block 413), an external transaction ID is allocated and the MMU to external ID mapping is stored (block 422). The external transaction ID may be allocated from the pool of available external transaction IDs for read requests and unlike the method described above with reference to FIGS. 3A and 3B, the same pool of external transaction IDs may be used for both cache originating and MMU originating memory read requests.

In an example, the external transaction ID may be allocated by the remapping logic in the read arbiter module 516R (described above). When a request has been selected by the read arbiter module 516R (in block 411), the remapping logic finds the first available free entry in the array for read requests. The MMU transaction ID is stored in this particular array entry and the entry number which has been assigned then forms the external transaction ID which is output onto the external bus 206 (in block 413).

Subsequently to issuing the MMU read request (in block 413), the read arbiter module 516R receives the data (in block 314) along with the external transaction ID. This external transaction ID is then mapped back to the internal ID, which in this case is a MMU transaction ID, and the external transaction ID is freed (block 425) e.g. using the array maintained by the remapping logic.

The read arbiter module 516R can identify from the MMU transaction ID that the data received (in block 314) relates to a memory request which was generated by the MMU 208. The read arbiter module 516R therefore passes the data to the MMU (block 320) and the MMU transaction ID is freed by the MMU 208. As described above, a single TLB miss may require multiple memory look-ups (e.g. in the case of nested translations) and so the read arbiter module 516R may receive further memory read requests (as indicated by the dotted arrow from block 320 to block 418) before the translation is available in the MMU for the cache originating read/write request.

Once the translation is available for a read request, the read transaction tracker module 514R receives the translation from the MMU or a pointer to the translation in the TLB along with the transaction ID to which the translation relates (block 310). As the translation is now ready, the memory read request (identified by the internal transaction ID allocated in block 404) is ready to be issued and so may be passed to the read arbiter module 516R.

The read arbiter module 516R selects a memory read request from those which are ready (block 411), allocates an external transaction ID and stores the internal to external transaction ID mapping (block 412) and issues it onto the external bus 206 (block 413) using the external transaction ID.

Subsequent to issuing a memory read request with a particular external transaction ID (in block 413), the read arbiter module 516R receives read data with a matching transaction ID (block 314). The read arbiter module 516R (e.g. the remapping logic, described above) maps the external transaction ID back to the internal transaction ID and frees the external transaction ID (block 415). Based on the internal transaction ID (which may be a MMU transaction ID or an internal read transaction ID), the read arbiter module 516R can determine if the memory request originated from the cache 204 or the MMU 208 and then forward the read data to the read transaction tracker module 514R (for cache originating requests) or the MMU 208 (for MMU originating requests).

As described above, once the read request is complete, the internal read transaction ID which was allocated to the cache originating read request (in block 404) can be freed (block 416). This means that the internal read transaction ID returns to the pool of available internal transaction IDs which can be allocated to another incoming read request from the cache (in block 404).

Once the translation is available for a write request, the write transaction tracker module 514W receives the translation from the MMU or a pointer to the translation in the TLB along with the transaction ID to which the translation relates (block 310). As the translation is now ready, the memory write request (identified by the internal transaction ID allocated in block 404) is ready to be issued and so may be passed to the write arbiter module 516W.

The write arbiter module 516W selects a memory write request from those which are ready (block 411), allocates an external transaction ID and stores the internal to external transaction ID mapping (block 412) and issues it onto the external bus 206 (block 413) using the external transaction ID.

Subsequent to issuing a memory write request with a particular external transaction ID (in block 413), the write arbiter module 516W receives a write response with a matching transaction ID (block 314). The write arbiter module 516W (e.g. the remapping logic, described above) maps the external transaction ID back to the internal transaction ID and frees the external transaction ID (block 415). The write arbiter module 516W forwards the write response to the write transaction tracker module 514W.

As described above, once the write request is complete, the internal write transaction ID which was allocated to the cache originating write request (in block 404) can be freed (block 416). This means that the internal write transaction ID returns to the pool of available internal transaction IDs which can be allocated to another incoming write request from the cache (in block 404).

In various examples, the converter module 202, 502 may also perform hazard checking, e.g. to check for data dependence between requests and then ensure that where such dependencies occur, the earlier memory request is performed before the later memory request which depends upon it. There are several types of hazards (which may also be called address or data hazards): read after write (RAW), write after read (WAR) and write after write (WAW). In a RAW hazard, the write must occur before the read or the wrong data will be read and in a WAR hazard, the write must occur after the read or again the wrong data will be read. In a WAW hazard, the writes must occur in the correct order or the data which is ultimately stored will not be correct. In some examples, read after read (RAR) hazards may also be considered (as described below). The hazard checking may be implemented within the assignment modules 212, 512R, 512W and/or the transaction tracker modules 214, 514R, 514W.

In order to implement hazard checking, a number of additional checks are introduced into the methods described above and where there are separate read and write paths (as in the hierarchy 500 in FIG. 5) the modules which implement the hazard checking in each path communicate (e.g. as indicated by the dotted arrows 520-524).

Figure 6:
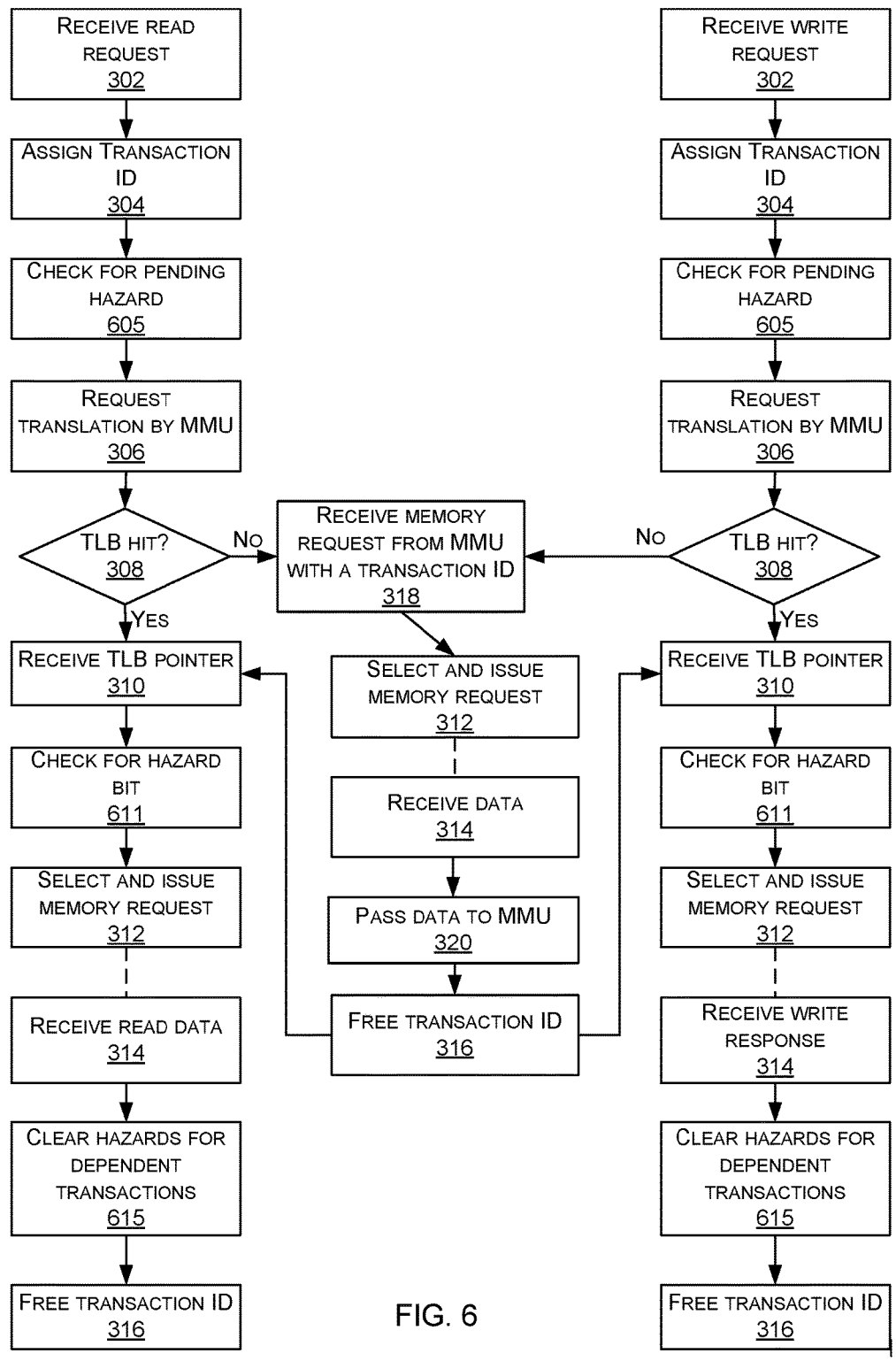
FIG. 6 is a flow diagram showing a fourth example method of operation of a converter module as described herein.
Figure 7:
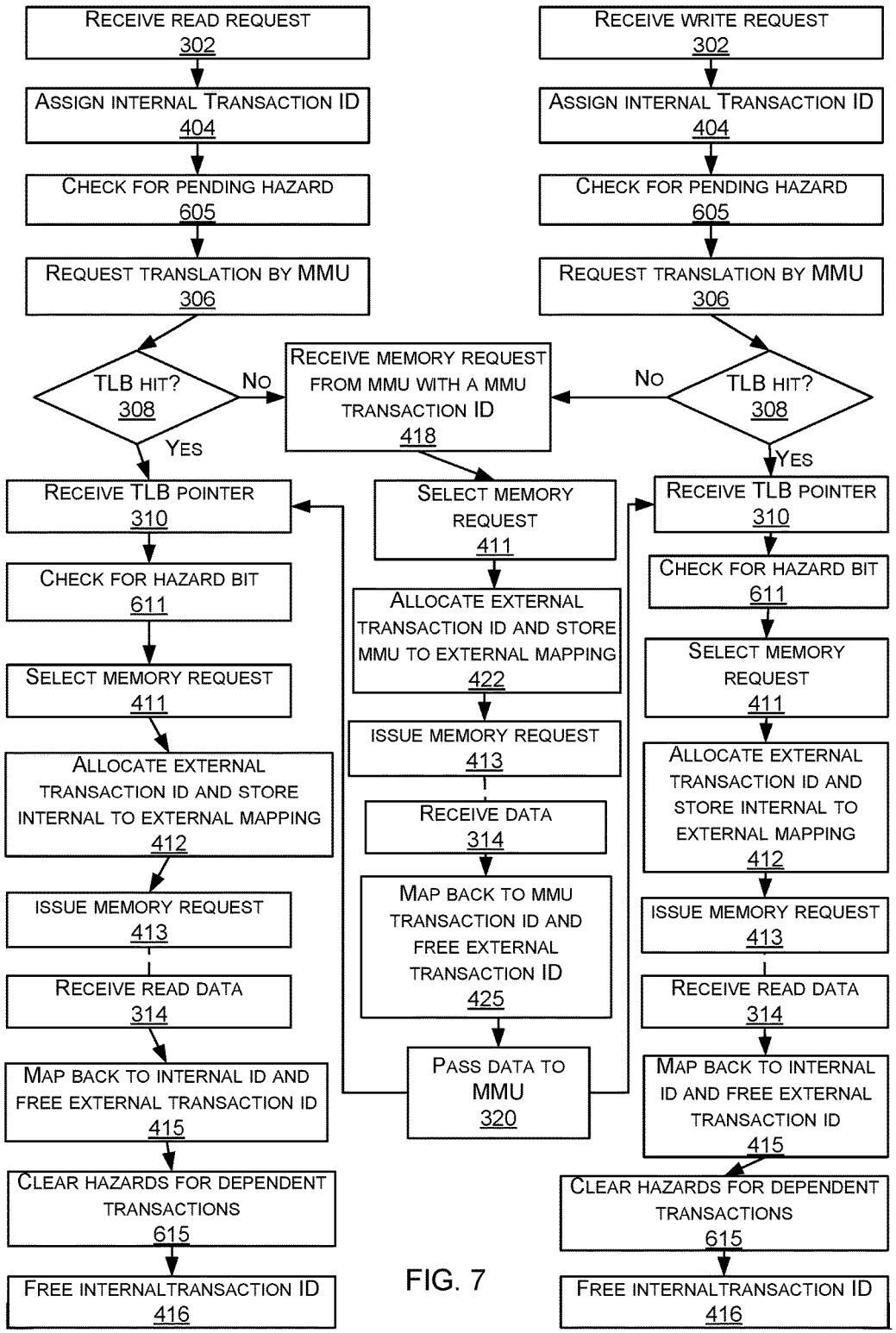
FIG. 7 is a flow diagram showing a fifth example method of operation of a converter module as described herein.

FIGS. 6 and 7 shows further example methods of operation of the converter module 502 in which hazard checking is performed. FIG. 6 is a variation of that shown in FIG. 3A and described above and FIG. 7 is a variation of that shown in FIG. 4 and described above; however, in FIGS. 6 and 7 the operation of the read and write paths have been shown separately. Furthermore, although FIGS. 6 and 7 show that in the event of a TLB miss, the pointer is not immediately received (as described above with reference to FIG. 3A), in variations of the methods shown in FIGS. 6 and 7, the pointer may still be received but it may point to an entry which is marked as outstanding (as described above with reference to FIG. 3B).

It can be seen from FIGS. 6 and 7 that there are three additional stages to the method (blocks 605, 611 and 615), although in other examples the same functionality may be implemented in a different number of additional stages or incorporated into existing stages. Firstly, after a transaction ID has been assigned (in block 304 or 404, where this may be an external transaction ID as in FIG. 6 or an internal transaction ID as in FIG. 7) a check is performed for a pending hazard (block 605). This check identifies if there are any transactions which are pending which need to be completed before the new transaction can be performed. A pending transaction is one which has been assigned a transaction ID and has not completed yet, so the transaction ID has not yet been cleared. A pending transaction may alternatively be referred to as an in-flight transaction.

As hazards can occur between a read and a write transaction (i.e. for RAW and WAR hazards), one path through the converter module 502 cannot perform the hazard check in isolation of the other path. Instead, to perform the hazard check (in block 605) the modules which implement the hazard checking (e.g. the transaction tracker modules 514R, 514W) need at least some information on all pending reads and all pending writes, irrespective of which path they are in. This information may be communicated between the modules that implement the hazard checking in each path (e.g. the transaction tracker modules 514R, 514W, as indicated by the dotted arrow 520 in FIG. 5) or alternatively, the modules may receive data about all incoming requests from the cache (e.g. from the assignment module 512R, 512W in the other path, as indicated by dotted arrows 522, 524).

If a pending hazard is identified for an incoming read request (in block 605) a bit (or flag) is set in the read transaction tracker module 514R in relation to that incoming request and the pending write request on which the incoming read request depends (as this is a RAW hazard) is tagged with the transaction ID of the read request by the write transaction tracker module 514W (also in block 605). If RAR hazards are also considered, and a RAR hazard is identified for an incoming read request, the pending read request on which the incoming read request depends is tagged with the transaction ID of the read request by the read transaction tracker module 514R (also in block 605).

If a pending hazard is identified for an incoming write request (in block 605) a bit (or flag) is set in the write transaction tracker module 514W in relation to that incoming request. In the case of a WAW hazard, the pending write request on which the incoming write request depends is tagged with the transaction ID of the write request by the write transaction tracker module 514W (also in block 605). In the case of a WAR hazard, the pending read request on which the incoming write request depends is tagged with the transaction ID of the write request by the read transaction tracker module 514R (also in block 605).

The tagging of pending requests (by the transaction tracker module 514R, 514W in block 605) may, for example, be implemented using a linked-list. For example, if an incoming memory request which has been allocated a transaction ID of '004' is identified as being dependent upon a pending memory request which has been allocated a transaction ID of '002' (in block 605), an entry is added to a linked-list in the transaction tracker module which is tracking memory request '002' (i.e. the read transaction tracker module 514R if the transaction with ID '002' is a read request and the write transaction tracker module 514W if the transaction with ID '002' is a write request) which links transaction '002' to transaction '004'. Consequently there may be two linked-lists, a read linked-list stored in the read transaction tracker module 514R and which stores details of any memory requests which depend upon an earlier read request and a write linked-list stored in the write transaction tracker module 514W and which stores details of any memory requests which depend upon an earlier write request.

In various examples, a single linked-list may be used which encompasses both reads and writes and therefore spans both the transaction tracker modules 514R, 514W (i.e. it is partially stored in each of the transaction tracker modules 514R, 514W and acts as a single combined linked-list).

In various examples, the linked-list (irrespective of whether there are one or two linked-lists) is limited so that there is only ever allowed to be a single request (either read or write) outstanding to a particular address because any further requests to the same address should always have an ordering dependency and will therefore be held off until earlier requests in the list complete. In such an implementation, RAR hazards are also included in the hazard checking because it simplifies the linked-list. If RAR hazards are excluded from the hazard checking (because allowing two reads to the same address to proceed in any order should not cause a problem), a subsequent write request to the same address would need both reads to complete before the write request's pending hazard bit can be cleared (as described below) and this adds complexity to both the linked-list and the bit clearing mechanism.

Whilst a transaction has the 'pending hazard' bit set in the relevant transaction tracker module (i.e. the read transaction tracker module 514R for read requests and the write transaction tracker module 514W for write requests), that memory request cannot be issued onto the external bus 206. In various examples, this means that the relevant transaction tracker module cannot output the memory request to the relevant arbiter module (i.e. the read arbiter module 516R for read requests and the write arbiter module 516W for write requests) until the 'pending hazard' bit has been cleared. The blocking of the issuance of such requests (which have the 'pending hazard' bit set) is implemented in the examples shown in FIGS. 6 and 7 by a check (block 611) prior to issuance of the memory request onto the external bus (in block 312 or 411). If the check (in block 611) determines that the 'pending hazard' bit is set for a memory request, that request is stalled until the 'pending hazard' bit is cleared.

The 'pending hazard' bit for a memory request is cleared once the pending request on which it depends has completed. Prior to, or at the same time as, freeing the transaction ID which was allocated by the relevant assignment module (i.e. the read assignment module 512R for read requests and the write assignment module 512W for write requests) a check is performed to identify any later, pending memory requests which depend on the request that has completed (block 615). Where a linked-list is used to record dependencies (in block 605), this list may be checked to identify any later, pending memory requests which depend on the request that has completed (in block 615).

If one or more pending memory requests are identified (in block 615), the pending hazard bit for those memory requests may be cleared (also in block 615) but only if those identified pending memory requests do not also depend upon another pending memory request. For example, if a memory request '003' depends upon two memory requests '002' and '001', then the pending hazard bit for memory request '003' cannot be cleared until both memory request '001' and memory request '002' have completed. Consequently, before clearing a pending hazard bit (in block 615), data in both the read transaction tracker module 514R and the write transaction tracker module 514W may be checked (e.g. both the read and write linked-lists may be checked). As described above, in various examples there is only a single linked-list and in various examples, the linked-list(s) may be limited to only allow one pending memory request to a single address in memory.

Where hazard checking is implemented (as described above), the early stages of the converter module 502 may operate in lockstep such that both transaction tracker modules 514R, 514W receive details about an incoming memory request from the cache 204 at the same time.

Figure 8:
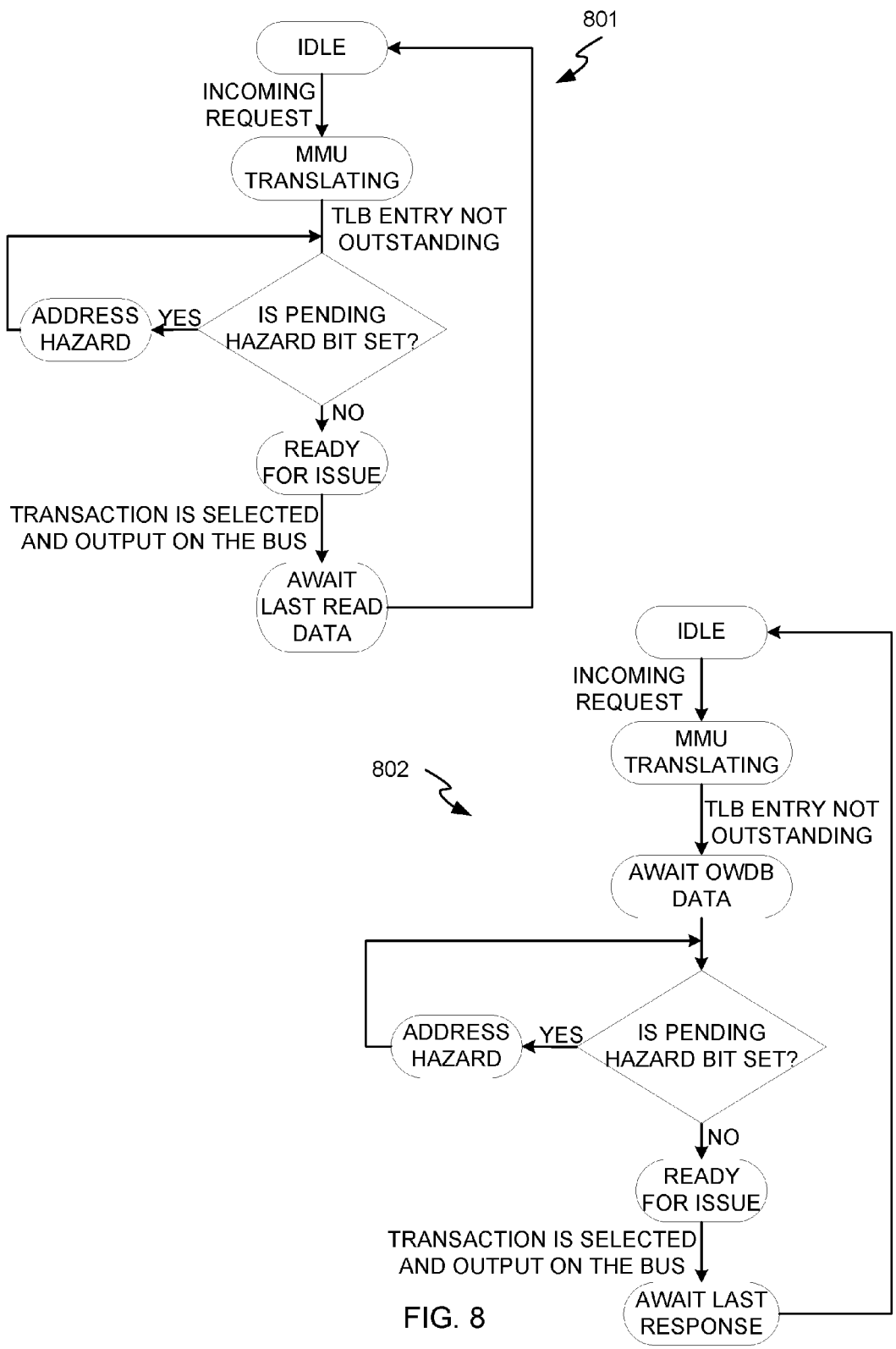
FIG. 8 shows two example state diagrams which may be implemented within a converter module as described herein.

As described above, the transaction tracker modules 214, 514R, 514W may track each transaction by storing a state of each pending read and/or write transaction. FIG. 8 shows two example state diagrams with the first state diagram 801 being for read transactions (as may be used by the transaction tracker module 214 in FIG. 2 or the read transaction tracker module 514R in FIG. 5) and the second state diagram 802 being for write transactions (as may be used by the transaction tracker module 214 in FIG. 2 or the write transaction tracker module 514W in FIG. 5). As can be seen from FIG. 8, in the read state diagram 801, there are 5 possible states and in the write state diagram 802 there are 6 possible states, because there is an extra state of waiting for the write data to be available ('AWAIT OWDB DATA'). It will be appreciated that these state diagrams are provided by way of example and in various examples there may be different numbers of possible states for read and/or write transactions in the state diagrams used.

It will be appreciated that the converter module 202, 502 described herein may be implemented in hardware logic and more specifically, the assignment modules 212, 512R, 512W, transaction tracker modules 214, 514R, 514W and arbiter modules 216, 516R, 514W may be implemented in hardware logic. For example, the transaction tracker modules 214, 514R, 514W may be implemented as an array of state machines (e.g. one per transaction ID) such that each transaction ID can effectively be tracked independently (e.g. as shown in FIGS. 3A, 3B, 4, 6 and 7).

The converter modules 202, 502 and memory hierarchies 200 500 which contain them may be used with any type of processor. In various examples, the processor may involve parallel computations and so may be a GPU (e.g. such that the cache 204 is a GPU L2 cache) or a multi-threaded CPU. Where the converter modules 202, 502 are used for processor which involve lots of parallel processing (such as a GPU), there are likely to be many memory requests to issue in the time taken to perform a MMU/TLB miss and so the methods described herein can improve performance and at least partially hide any latency involved with the MMU/TLB miss.

In the methods described above with reference to FIGS. 4 and 7, it may only be necessary to have sufficient external transaction IDs to cover the round-trip processing time of the external bus 206 and the external memory which is connected to that bus. Whilst the number of internal transaction IDs may be the same as the number of external transaction IDs, as described above the performance (e.g. the efficiency) of the memory hierarchy may be improved by providing a larger number of internal transaction IDs at the expense of a larger memory for tracking the state of pending transactions within the transaction tracker modules 214, 514R, 514W.

In the above description, the assignment module 212, 512R, 512W only assigns transaction IDs to incoming memory requests which result from cache misses. In various examples, the transaction IDs may be applied earlier such that transaction IDs (whether internal as described with reference to FIGS. 3A, 3B and 6 or external as described with reference to FIGS. 4 and 7) are assigned to all memory requests issued by the processor (e.g. by the GPU). This, however, requires many more transaction IDs to be available or memory requests will be stalled because there are no available transaction IDs to be assigned by the assignment module 212, 512R, 512W.

Figure 9:
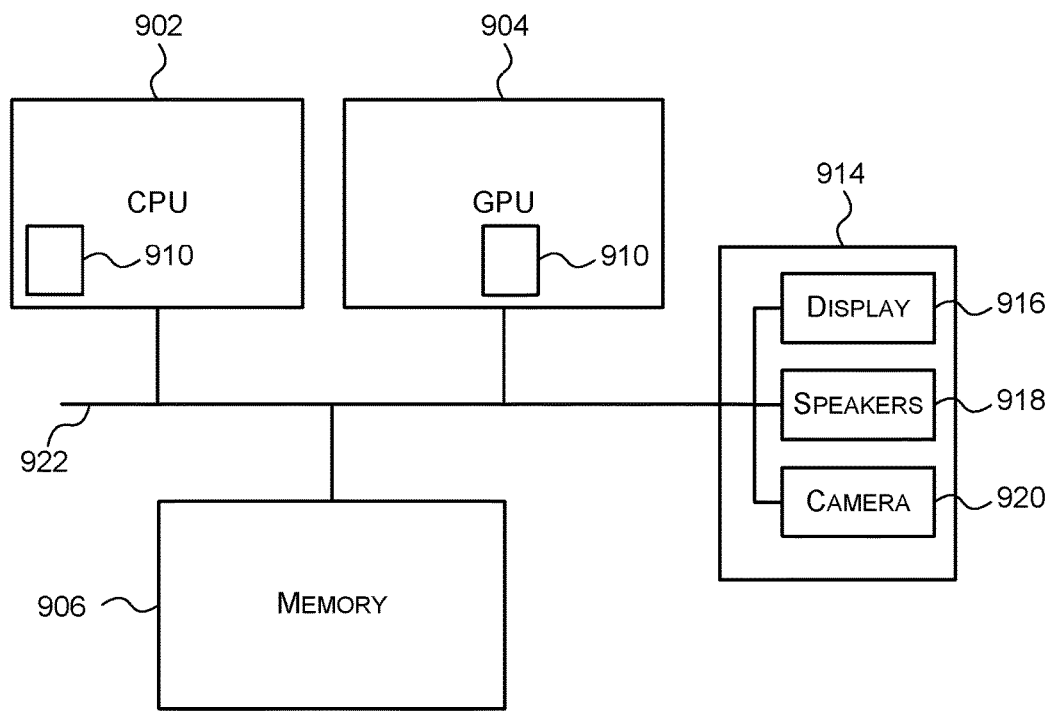
FIG. 9 shows a computer system in which a converter module described herein is implemented.

FIG. 9 shows a computer system in which the converter described herein may be implemented. The computer system comprises a CPU 902, a GPU 904, a memory 906 and other devices 914, such as a display 916, speakers 918 and a camera 920. The converter module 910 may be implemented in the CPU 902 and/or GPU 904. The components of the computer system can communicate with each other via a communications bus 922.

The converter modules 202, 502 of FIGS. 2 and 5 are shown as comprising a number of functional blocks. This is schematic only and is not intended to define a strict division between different logic elements of such entities. Each functional block may be provided in any suitable manner. It is to be understood that intermediate values described herein as being formed by a functional block need not be physically generated by the converter module at any point and may merely represent logical values which conveniently describe the processing performed by the converter module between its input and output.

A first further example provides a module comprising: an assignment module arranged to receive memory requests from a cache (204) and to assign a transaction identifier to each received memory request, wherein the memory requests received from the cache include one or more memory addresses defined in a virtual address space; a transaction tracker module arranged to receive a memory request from the assignment module with the assigned transaction identifier, to track the status of the memory request and to receive translation information from a memory management unit (208), wherein the translation information comprises a translation of a virtual memory address in the memory request to a physical memory address or a pointer to the translation; and an arbiter module arranged to receive a memory request from the transaction tracker module with the assigned transaction identifier when the memory request is ready for issue and to issue the memory request to a memory via an external bus and to trigger the freeing of the assigned transaction identifier in response to receiving a response from the memory via the external bus, wherein the memory request issued to memory includes one or more physical memory addresses determined using the translation information.

The arbiter module may be further arranged to receive a plurality of memory requests and to select a memory request to issue from any received memory requests which have not yet been issued. The arbiter module may be further arranged to receive a memory read request from the memory management unit with a transaction identifier assigned by the memory management unit and to select the memory read request from the memory management unit for issue ahead of any memory requests received from the transaction tracker module which have not yet been issued. The arbiter module may be arranged to select a memory request to issue from any received memory requests which have not yet been issued according to pre-defined rules. The pre-defined rules may cause the selection of a memory request received from the memory management unit ahead of a memory request received from the transaction tracker module and if there is not a memory request received from the memory management unit, selection of a memory request received from the transaction tracker module based at least in part on a time of receipt of the translation information for the memory requests.

The transaction identifiers assigned by the assignment module may be external transaction identifiers and wherein the arbiter module may be arranged to issue memory requests using the assigned external transaction identifiers.

The arbiter module may be arranged, in response to receiving a response from the memory via the external bus, the response comprising an external transaction identifier, to identify the unit from which the corresponding request with the same external transaction identifier was received and to transmit the response to the identified unit, wherein the unit comprises the transaction tracker module or the memory management unit.

The transaction identifiers assigned by the assignment module may be internal transaction identifiers and wherein the arbiter module is further arranged, following selection of a memory request for issue, to allocate an external transaction identifier to the memory request and store a mapping between the assigned internal transaction identifier and the allocated external transaction identifier and wherein the arbiter module is arranged to issue memory requests using the allocated external transaction identifiers. The arbiter module may be arranged, in response to receiving a response from the memory via the external bus, the response comprising an external transaction identifier, to map the external transaction identifier back to the assigned internal transaction identifier, identify the unit from which the corresponding request with the same internal transaction identifier was received and to transmit the response to the identified unit, wherein the unit comprises the transaction tracker module or the memory management unit.

The module may comprise a read path arranged to receive memory read requests from the cache and a write path arranged to receive memory write requests from the cache, wherein the read path comprises the assignment module, the transaction tracker module and the arbiter module and wherein the write path comprises a second assignment module, a second transaction tracker module and a second arbiter module. The transaction tracker module and the second transaction tracker module may both be arranged to check incoming memory requests from the cache for data hazards and in response to detecting a hazard, to set a flag for the incoming transaction and wherein a memory request is not ready for issue if the flag is set. The transaction tracker module and the second transaction tracker module may both be arranged to clear the flag for a memory request which depends upon an earlier memory request in response to receiving a response from the memory via the external bus for the earlier memory request.

A second further example provides a method comprising: receiving memory requests from a cache at a converter module; assigning, in the converter module, a transaction identifier to each received memory request, wherein the memory requests received from the cache include one or more memory addresses defined in a virtual address space; tracking, in the converter module, the status of the memory requests; receiving, in the converter module, translation information from a memory management unit, wherein the translation information comprises a translation of a virtual memory address in one of the memory requests to a physical memory address or a pointer to the translation; issuing said one of the memory requests from the converter module to a memory via an external bus, wherein the memory request issued to memory includes one or more physical memory addresses determined using the translation information; and triggering the freeing of the assigned transaction identifier in response to receiving a response from the memory via the external bus.

The method may further comprise: selecting a memory request to issue from any received memory requests which have not yet been issued. The method may further comprise: receiving a memory read request from the memory management unit with a transaction identifier assigned by the memory management unit, and wherein selecting a memory request comprises selecting a memory read request received from the memory management unit for issue ahead of any memory requests received from the cache. A memory request may be selected to issue according to pre-defined rules. The pre-defined rules may cause the selection of a memory request received from the memory management unit ahead of a memory request received from the cache and if there is not a memory request received from the memory management unit, selection of a memory request received from the cache based at least in part on a time of receipt of the translation information for the memory requests.

The transaction identifiers assigned may be external transaction identifiers and memory requests are issued using the assigned external transaction identifiers.

The transaction identifiers assigned may be internal transaction identifiers and wherein the method may further comprise, following selection of a memory request for issue: allocating an external transaction identifier to the memory request; and storing a mapping between the assigned internal transaction identifier and the allocated external transaction identifier, and wherein memory requests are issued using the allocated external transaction identifiers. The method may further comprise: in response to receiving a response from the memory via the external bus, the response comprising an external transaction identifier, mapping the external transaction identifier back to the assigned internal transaction identifier.

The method may further comprise: checking memory requests received from the cache for data hazards; and in response to detecting a hazard, setting a flag for the incoming request and wherein a memory request cannot be issued if the flag is set. The method may further comprise: clearing a flag for a memory request which depends upon an earlier memory request in response to receiving a response from the memory via the external bus for the earlier memory request (615).

A third aspect provides a system comprising: a processor arranged to assign a transaction identifier to each memory request issued by the processor; and a module comprising: an assignment module arranged to receive memory requests from a cache, wherein the memory requests received from the cache include a transaction identifier assigned by the processor and one or more memory addresses defined in a virtual address space; a transaction tracker module arranged to receive a memory request from the assignment module with the assigned transaction identifier, to track the status of the memory request and to receive translation information from a memory management unit, wherein the translation information comprises a translation of a virtual memory address in the memory request to a physical memory address or a pointer to the translation; and an arbiter module arranged to receive a memory request from the transaction tracker module with the assigned transaction identifier when the memory request is ready for issue and to issue the memory request to a memory via an external bus and to trigger the freeing of the assigned transaction identifier in response to receiving a response from the memory via the external bus, wherein the memory request issued to memory includes one or more physical memory addresses determined using the translation information.

A fourth aspect provides a method comprising: assigning, in a processor, a transaction identifier to each issued memory request; receiving memory requests from a cache at a converter module; wherein the memory requests received from the cache include a transaction identifier assigned by the processor and one or more memory addresses defined in a virtual address space; tracking, in the converter module, the status of the memory request; receiving, in the converter module, translation information from a memory management unit, wherein the translation information comprises a translation of a virtual memory address in the memory request to a physical memory address or a pointer to the translation; issuing the memory request from the converter module to a memory via an external bus, wherein the memory request issued to memory includes one or more physical memory addresses determined using the translation information; and triggering the freeing of the assigned transaction identifier in response to receiving a response from the memory via the external bus.

A fifth aspect provides an integrated circuit manufacturing system comprising: a non-transitory computer readable storage medium having stored thereon a computer readable description of an integrated circuit that describes a graphics processing system; a layout processing system configured to process the integrated circuit description so as to generate a circuit layout description of an integrated circuit embodying the graphics processing system; and an integrated circuit generation system configured to manufacture the graphics processing system according to the circuit layout description, wherein the processing system comprises a module as described herein.

Further aspects provide: a processing system configured to perform any of the methods described herein; a processing system comprising a module as described herein embodied in hardware on an integrated circuit; computer readable code adapted to perform the steps of any of the methods described herein when the code is run on a computer; a computer readable storage medium having encoded thereon the computer readable code; a method of manufacturing, at an integrated circuit manufacturing system, a processing system comprising a module as described herein; an integrated circuit definition dataset that, when processed in an integrated circuit manufacturing system, configures the system to manufacture a processing system comprising a module as described herein; and a computer readable storage medium having stored thereon a computer readable description of an integrated circuit that, when processed in an integrated circuit manufacturing system, causes the integrated circuit manufacturing system to manufacture a processing system comprising a module as described herein.

The converter module described herein may be embodied in hardware on an integrated circuit. The converter module described herein may be configured to perform any of the methods described herein. Generally, any of the functions, methods, techniques or components described above can be implemented in software, firmware, hardware (e.g., fixed logic circuitry), or any combination thereof. The terms "module," "functionality," "component", "element", "unit", "block" and "logic" may be used herein to generally represent software, firmware, hardware, or any combination thereof. In the case of a software implementation, the module, functionality, component, element, unit, block or logic represents program code that performs the specified tasks when executed on a processor. The algorithms and methods described herein could be performed by one or more processors executing code that causes the processor(s) to perform the algorithms/methods. Examples of a computer-readable storage medium include a random-access memory (RAM), read-only memory (ROM), an optical disc, flash memory, hard disk memory, and other memory devices that may use magnetic, optical, and other techniques to store instructions or other data and that can be accessed by a machine.

The terms computer program code and computer readable instructions as used herein refer to any kind of executable code for processors, including code expressed in a machine language, an interpreted language or a scripting language. Executable code includes binary code, machine code, bytecode, code defining an integrated circuit (such as a hardware description language or netlist), and code expressed in a programming language code such as C, Java or OpenCL. Executable code may be, for example, any kind of software, firmware, script, module or library which, when suitably executed, processed, interpreted, compiled, executed at a virtual machine or other software environment, cause a processor of the computer system at which the executable code is supported to perform the tasks specified by the code.

A processor, computer, or computer system may be any kind of device, machine or dedicated circuit, or collection or portion thereof, with processing capability such that it can execute instructions. A processor may be any kind of general purpose or dedicated processor, such as a CPU, GPU, System-on-chip, state machine, media processor, an application-specific integrated circuit (ASIC), a programmable logic array, a field-programmable gate array (FPGA), physics processing units (PPUs), radio processing units (RPUs), digital signal processors (DSPs), general purpose processors (e.g. a general purpose GPU), microprocessors, any processing unit which is designed to accelerate tasks outside of a CPU, etc. A computer or computer system may comprise one or more processors. Those skilled in the art will realize that such processing capabilities are incorporated into many different devices and therefore the term 'computer' includes set top boxes, media players, digital radios, PCs, servers, mobile telephones, personal digital assistants and many other devices.

It is also intended to encompass software which defines a configuration of hardware as described herein, such as HDL (hardware description language) software, as is used for designing integrated circuits, or for configuring programmable chips, to carry out desired functions. That is, there may be provided a computer readable storage medium having encoded thereon computer readable program code in the form of an integrated circuit definition dataset that when processed in an integrated circuit manufacturing system configures the system to manufacture a converter module configured to perform any of the methods described herein, or to manufacture a processor and/or cache hierarchy comprising any apparatus described herein. An integrated circuit definition dataset may be, for example, an integrated circuit description.

An integrated circuit definition dataset may be in the form of computer code, for example as a netlist, code for configuring a programmable chip, as a hardware description language defining an integrated circuit at any level, including as register transfer level (RTL) code, as high-level circuit representations such as Verilog or VHDL, and as low-level circuit representations such as OASIS (RTM) and GDSII. Higher level representations which logically define an integrated circuit (such as RTL) may be processed at a computer system configured for generating a manufacturing definition of an integrated circuit in the context of a software environment comprising definitions of circuit elements and rules for combining those elements in order to generate the manufacturing definition of an integrated circuit so defined by the representation. As is typically the case with software executing at a computer system so as to define a machine, one or more intermediate user steps (e.g. providing commands, variables etc.) may be required in order for a computer system configured for generating a manufacturing definition of an integrated circuit to execute code defining an integrated circuit so as to generate the manufacturing definition of that integrated circuit.

An example of processing an integrated circuit definition dataset at an integrated circuit manufacturing system so as to configure the system to manufacture a converter module or a processor comprising a converter module, as described above will now be described with respect to FIG. 10.

Figure 10:
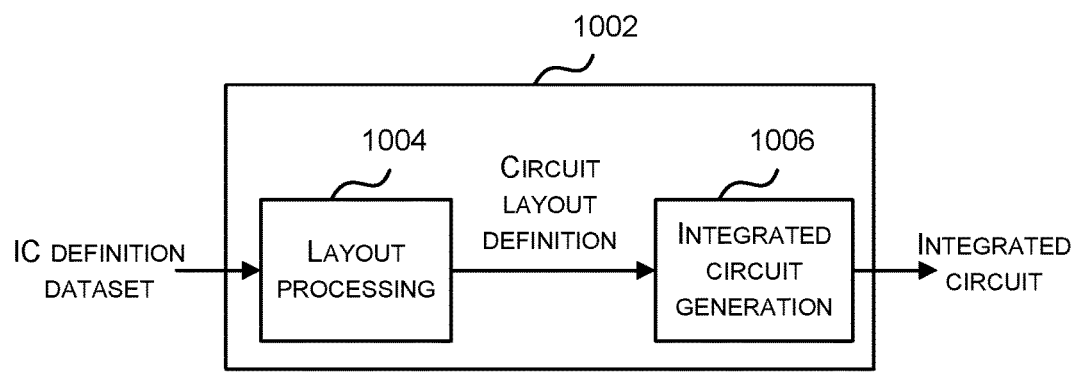
FIG. 10 shows an example of an integrated circuit manufacturing system which comprises a layout processing system and an integrated circuit generation system.

FIG. 10 shows an example of an integrated circuit (IC) manufacturing system 1002 which comprises a layout processing system 1004 and an integrated circuit generation system 1006. The IC manufacturing system 1002 is configured to receive an IC definition dataset (e.g. defining a converter module 202, 502 as described in any of the examples herein or a processor comprising such a converter module), process the IC definition dataset, and generate an IC according to the IC definition dataset (e.g. which embodies a converter module as described in any of the examples herein or a processor comprising such a converter module). The processing of the IC definition dataset configures the IC manufacturing system 1002 to manufacture an integrated circuit embodying a converter module (or a processor comprising the converter module) as described in any of the examples herein. More specifically, the layout processing system 1004 is configured to receive and process the IC definition dataset to determine a circuit layout.

Methods of determining a circuit layout from an IC definition dataset are known in the art, and for example may involve synthesizing RTL code to determine a gate level representation of a circuit to be generated, e.g. in terms of logical components (e.g. NAND, NOR, AND, OR, MUX and FLIP-FLOP components). A circuit layout can be determined from the gate level representation of the circuit by determining positional information for the logical components. This may be done automatically or with user involvement in order to optimise the circuit layout. When the layout processing system 1004 has determined the circuit layout it may output a circuit layout definition to the IC generation system 1006.

The IC generation system 1006 generates an IC according to the circuit layout definition, as is known in the art. For example, the IC generation system 1006 may implement a semiconductor device fabrication process to generate the IC, which may involve a multiple-step sequence of photo lithographic and chemical processing steps during which electronic circuits are gradually created on a wafer made of semiconducting material. The circuit layout definition may be in the form of a mask which can be used in a lithographic process for generating an IC according to the circuit definition. Alternatively, the circuit layout definition provided to the IC generation system 1006 may be in the form of computer-readable code which the IC generation system 1006 can use to form a suitable mask for use in generating an IC.

The different processes performed by the IC manufacturing system 1002 may be implemented all in one location, e.g. by one party. Alternatively, the IC manufacturing system 1002 may be a distributed system such that some of the processes may be performed at different locations, and may be performed by different parties. For example, some of the stages of: (I) synthesizing RTL code representing the IC definition dataset to form a gate level representation of a circuit to be generated, (ii) generating a circuit layout based on the gate level representation, (iii) forming a mask in accordance with the circuit layout, and (iv) fabricating an integrated circuit using the mask, may be performed in different locations and/or by different parties.

In other examples, processing of the integrated circuit definition dataset at an integrated circuit manufacturing system may configure the system to manufacture a converter module (or a processor comprising the converter module) without the IC definition dataset being processed so as to determine a circuit layout. For instance, an integrated circuit definition dataset may define the configuration of a reconfigurable processor, such as an FPGA, and the processing of that dataset may configure an IC manufacturing system to generate a reconfigurable processor having that defined configuration (e.g. by loading configuration data to the FPGA).

In some examples, an integrated circuit definition dataset could include software which runs on hardware defined by the dataset or in combination with hardware defined by the dataset. In the example shown in FIG. 10, the IC generation system may further be configured by an integrated circuit definition dataset to, on manufacturing an integrated circuit, load firmware onto that integrated circuit in accordance with program code defined at the integrated circuit definition dataset or otherwise provide program code with the integrated circuit for use with the integrated circuit.

Those skilled in the art will realize that storage devices utilized to store program instructions can be distributed across a network. For example, a remote computer may store an example of the process described as software. A local or terminal computer may access the remote computer and download a part or all of the software to run the program. Alternatively, the local computer may download pieces of the software as needed, or execute some software instructions at the local terminal and some at the remote computer (or computer network). Those skilled in the art will also realize that by utilizing conventional techniques known to those skilled in the art that all, or a portion of the software instructions may be carried out by a dedicated circuit, such as a DSP, programmable logic array, or the like.

The methods described herein may be performed by a computer configured with software in machine readable form stored on a tangible storage medium e.g. in the form of a computer program comprising computer readable program code for configuring a computer to perform the constituent portions of described methods or in the form of a computer program comprising computer program code means adapted to perform all the steps of any of the methods described herein when the program is run on a computer and where the computer program may be embodied on a computer readable storage medium. Examples of tangible (or non-transitory) storage media include disks, thumb drives, memory cards etc. and do not include propagated signals. The software can be suitable for execution on a parallel processor or a serial processor such that the method steps may be carried out in any suitable order, or simultaneously.

The hardware components described herein may be generated by a non-transitory computer readable storage medium having encoded thereon computer readable program code.

Memories storing machine executable data for use in implementing disclosed aspects can be non-transitory media. Non-transitory media can be volatile or non-volatile. Examples of volatile non-transitory media include semiconductor-based memory, such as SRAM or DRAM. Examples of technologies that can be used to implement non-volatile memory include optical and magnetic memory technologies, flash memory, phase change memory, resistive RAM.

A particular reference to "logic" refers to structure that performs a function or functions. An example of logic includes circuitry that is arranged to perform those function (s). For example, such circuitry may include transistors and/or other hardware elements available in a manufacturing process. Such transistors and/or other elements may be used to form circuitry or structures that implement and/or contain memory, such as registers, flip flops, or latches, logical operators, such as Boolean operations, mathematical operators, such as adders, multipliers, or shifters, and interconnect, by way of example. Such elements may be provided as custom circuits or standard cell libraries, macros, or at other levels of abstraction. Such elements may be interconnected in a specific arrangement. Logic may include circuitry that is fixed function and circuitry can be programmed to perform a function or functions; such programming may be provided from a firmware or software update or control mechanism. Logic identified to perform one function may also include logic that implements a constituent function or sub-process. In an example, hardware logic has circuitry that implements a fixed function operation, or operations, state machine or process.

Any range or device value given herein may be extended or altered without losing the effect sought, as will be apparent to the skilled person.

It will be understood that the benefits and advantages described above may relate to one embodiment or may relate to several embodiments. The embodiments are not limited to those that solve any or all of the stated problems or those that have any or all of the stated benefits and advantages.

Any reference to 'an' item refers to one or more of those items. The term 'comprising' is used herein to mean including the method blocks or elements identified, but that such blocks or elements do not comprise an exclusive list and an apparatus may contain additional blocks or elements and a method may contain additional operations or elements. Furthermore, the blocks, elements and operations are themselves not impliedly closed.

The steps of the methods described herein may be carried out in any suitable order, or simultaneously where appropriate. The arrows between boxes in the figures show one example sequence of method steps but are not intended to exclude other sequences or the performance of multiple steps in parallel. Additionally, individual blocks may be deleted from any of the methods without departing from the spirit and scope of the subject matter described herein. Aspects of any of the examples described above may be combined with aspects of any of the other examples described to form further examples without losing the effect sought. Where elements of the figures are shown connected by arrows, it will be appreciated that these arrows show just one example flow of communications (including data and control messages) between elements. The flow between elements may be in either direction or in both directions.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein. In view of the foregoing description it will be evident to a person skilled in the art that various modifications may be made within the scope of the invention.

The invention claimed is:

1. A module comprising:
an assignment module arranged to receive memory requests from a cache and to assign a transaction identifier to each received memory request, wherein the memory requests received from the cache include one or more memory addresses defined in a virtual address space;
a transaction tracker module arranged to receive a memory request from the assignment module with the assigned transaction identifier, to track the status of the memory request and to receive translation information from a memory management unit, wherein the translation information comprises a translation of a virtual memory address in the memory request to a physical memory address or a pointer to the translation; and
an arbiter module arranged to receive a memory request from the transaction tracker module with the assigned transaction identifier when the memory request is ready for issue and to issue the memory request to a memory via an external bus and to trigger the freeing of the assigned transaction identifier in response to receiving a response from the memory via the external bus, wherein the memory request issued to memory includes one or more physical memory addresses determined using the translation information.

2. A module according to claim 1, wherein the arbiter module is further arranged to receive a plurality of memory requests and to select a memory request to issue from any received memory requests which have not yet been issued.

3. A module according to claim 2, wherein the arbiter module is further arranged to receive a memory read request from the memory management unit with a transaction identifier assigned by the memory management unit and to select the memory read request from the memory management unit for issue ahead of any memory requests received from the transaction tracker module which have not yet been issued.

4. A module according to claim 2, wherein the arbiter module is arranged to select a memory request to issue from any received memory requests which have not yet been issued according to pre-defined rules; and optionally wherein the pre-defined rules cause the selection of a memory request received from the memory management unit ahead of a memory request received from the transaction tracker module and if there is not a memory request received from the memory management unit, selection of a memory request received from the transaction tracker module based at least in part on a time of receipt of the translation information for the memory requests.

5. A module according to claim 1, wherein the transaction identifiers assigned by the assignment module are external transaction identifiers and wherein the arbiter module is arranged to issue memory requests using the assigned external transaction identifiers.

6. A module according to claim 5, wherein the arbiter module is arranged, in response to receiving a response from the memory via the external bus, the response comprising an external transaction identifier, to identify the unit from which the corresponding request with the same external transaction identifier was received and to transmit the response to the identified unit, wherein the unit comprises the transaction tracker module or the memory management unit.

7. A module according to claim 1, wherein the transaction identifiers assigned by the assignment module are internal transaction identifiers and wherein the arbiter module is further arranged, following selection of a memory request for issue, to allocate an external transaction identifier to the memory request and store a mapping between the assigned internal transaction identifier and the allocated external transaction identifier and wherein the arbiter module is arranged to issue memory requests using the allocated external transaction identifiers.

8. A module according to claim 7, wherein the arbiter module is arranged, in response to receiving a response from the memory via the external bus, the response comprising an external transaction identifier, to map the external transaction identifier back to the assigned internal transaction identifier, identify the unit from which the corresponding request with the same internal transaction identifier was received and to transmit the response to the identified unit, wherein the unit comprises the transaction tracker module or the memory management unit.

9. A module according to claim 1, comprising a read path arranged to receive memory read requests from the cache and a write path arranged to receive memory write requests from the cache, wherein the read path comprises the assignment module, the transaction tracker module and the arbiter module and wherein the write path comprises a second assignment module, a second transaction tracker module and a second arbiter module.

10. A module according to claim 9, wherein the transaction tracker module and the second transaction tracker module are both arranged to check incoming memory requests from the cache for data hazards and in response to detecting a hazard, to set a flag for the incoming transaction and wherein a memory request is not ready for issue if the flag is set; and optionally wherein the transaction tracker module and the second transaction tracker module are arranged to clear the flag for a memory request which depends upon an earlier memory request in response to receiving a response from the memory via the external bus for the earlier memory request.

11. A method comprising:
receiving memory requests from a cache at a converter module;
assigning, in the converter module, a transaction identifier to each received memory request, wherein the memory requests received from the cache include one or more memory addresses defined in a virtual address space;
tracking, in the converter module, the status of the memory requests;
receiving, in the converter module, translation information from a memory management unit, wherein the translation information comprises a translation of a virtual memory address in one of the memory requests to a physical memory address or a pointer to the translation;
issuing said one of the memory requests from the converter module to a memory via an external bus, wherein the memory request issued to memory includes one or more physical memory addresses determined using the translation information; and
triggering the freeing of the assigned transaction identifier in response to receiving a response from the memory via the external bus.

12. A method according to claim 11, further comprising:
selecting a memory request to issue from any received memory requests which have not yet been issued; and optionally,
receiving a memory read request from the memory management unit with a transaction identifier assigned by the memory management unit, and wherein selecting a memory request comprises selecting a memory read request received from the memory management unit for issue ahead of any memory requests received from the cache.

13. A method according to claim 11, wherein a memory request is selected to issue according to pre-defined rules and optionally wherein the pre-defined rules cause the selection of a memory request received from the memory management unit ahead of a memory request received from the cache and if there is not a memory request received from the memory management unit, selection of a memory request received from the cache based at least in part on a time of receipt of the translation information for the memory requests.

14. A method according to claim 11, wherein the transaction identifiers assigned are external transaction identifiers and memory requests are issued using the assigned external transaction identifiers.

15. A method according to claim 11, wherein the transaction identifiers assigned are internal transaction identifiers and wherein the method further comprises, following selection of a memory request for issue:
allocating an external transaction identifier to the memory request; and
storing a mapping between the assigned internal transaction identifier and the allocated external transaction identifier,
and wherein memory requests are issued using the allocated external transaction identifiers.

16. A method according to claim 15, further comprising:
in response to receiving a response from the memory via the external bus, the response comprising an external transaction identifier, mapping the external transaction identifier back to the assigned internal transaction identifier.

17. A method according to claim 11, further comprising:
checking memory requests received from the cache for data hazards; and
in response to detecting a hazard, setting a flag for the incoming request and wherein a memory request cannot be issued if the flag is set.

18. A method according to claim 17, further comprising:
clearing a flag for a memory request which depends upon an earlier memory request in response to receiving a response from the memory via the external bus for the earlier memory request.

19. A system comprising:
a processor arranged to assign a transaction identifier to each memory request issued by the processor; and
a module comprising:
an assignment module arranged to receive memory requests from a cache, wherein the memory requests received from the cache include a transaction identifier assigned by the processor and one or more memory addresses defined in a virtual address space;
a transaction tracker module arranged to receive a memory request from the assignment module with the assigned transaction identifier, to track the status of the memory request and to receive translation information from a memory management unit, wherein the translation information comprises a translation of a virtual memory address in the memory request to a physical memory address or a pointer to the translation; and
an arbiter module arranged to receive a memory request from the transaction tracker module with the assigned transaction identifier when the memory request is ready for issue and to issue the memory request to a memory via an external bus and to trigger the freeing of the assigned transaction identifier in response to receiving a response from the memory via the external bus, wherein the memory request issued to memory includes one or more physical memory addresses determined using the translation information.

20. A method comprising:

assigning, in a processor, a transaction identifier to each issued memory request;

receiving memory requests from a cache at a converter module, wherein the memory requests received from the cache include a transaction identifier assigned by the processor and one or more memory addresses defined in a virtual address space;

tracking, in the converter module, the status of the memory request;

receiving, in the converter module, translation information from a memory management unit, wherein the translation information comprises a translation of a virtual memory address in the memory request to a physical memory address or a pointer to the translation;

issuing the memory request from the converter module to a memory via an external bus, wherein the memory request issued to memory includes one or more physical memory addresses determined using the translation information; and triggering the freeing of the assigned transaction identifier in response to receiving a response from the memory via the external bus.

* * * * *